(12) United States Patent
Rosenthal et al.

(10) Patent No.: US 12,357,451 B2
(45) Date of Patent: *Jul. 15, 2025

(54) MINIMALLY INVASIVE NASAL IMPLANTS AND SYSTEMS AND METHODS

(71) Applicant: Spirox, Inc., Plymouth, MN (US)

(72) Inventors: Michael H. Rosenthal, Menlo Park, CA (US); Donald A. Gonzales, Austin, TX (US); Brian Domecus, San Francisco, CA (US); Scott J. Baron, Menlo Park, CA (US); Sergio Salinas, Redwood City, CA (US)

(73) Assignee: Stryker Corporation, Portage, MI (US)

( * ) Notice: Subject to any disclaimer, the term of this patent is extended or adjusted under 35 U.S.C. 154(b) by 250 days.

This patent is subject to a terminal disclaimer.

(21) Appl. No.: 17/355,404

(22) Filed: Jun. 23, 2021

(65) Prior Publication Data

US 2021/0315689 A1   Oct. 14, 2021

Related U.S. Application Data

(63) Continuation of application No. 16/346,048, filed as application No. PCT/US2017/059983 on Nov. 3, 2017, now Pat. No. 11,071,623.

(Continued)

(51) Int. Cl.
*A61F 2/18* (2006.01)
*A61B 17/24* (2006.01)
(Continued)

(52) U.S. Cl.
CPC .............. *A61F 2/186* (2013.01); *A61B 17/24* (2013.01); *A61B 17/320068* (2013.01);
(Continued)

(58) Field of Classification Search
CPC .. A61F 2/186; A61B 17/24; A61B 17/320016
See application file for complete search history.

(56) References Cited

U.S. PATENT DOCUMENTS 6,018,288 A   1/2000   Waite et al.
6,106,541 A   8/2000   Hurbis
(Continued)

FOREIGN PATENT DOCUMENTS

EP   1475056   10/2010
EP   2692313 A2   2/2014

OTHER PUBLICATIONS

PCT International Search Report for PCT/US2017/059983, Applicant: The Regents of the University of California, PCT/ISA/210 and 220, dated Aug. 31, 2008 (5 pages).

(Continued)

*Primary Examiner* — Suzette J Gherbi
(74) *Attorney, Agent, or Firm* — McDonnell Boehnen Hulbert & Berghoff LLP

(57) ABSTRACT

Nasal implants and nasal implant delivery tools are described herein. The nasal implants and tools can be used to deliver the implant in a minimally invasive way. The delivery tools can be adapted to separate the upper lateral cartilage from the septum and to place an implant between the septum and the upper lateral cartilage. The implant can be configured to be placed between the upper lateral cartilage and the septum. The implant system can include a first longitudinal body adapted to engage with upper lateral cartilage and the septum on a first side of the septum and a second longitudinal body adapted to engage with upper lateral cartilage and the septum on a second side of the septum.

20 Claims, 22 Drawing Sheets

Related U.S. Application Data

(60) Provisional application No. 62/417,055, filed on Nov. 3, 2016.

(51) Int. Cl.
*A61B 17/32* (2006.01)
*A61B 17/3207* (2006.01)

(52) U.S. Cl.
CPC ............ *A61B 17/320016* (2013.01); *A61B 2017/320056* (2013.01); *A61B 17/320725* (2013.01); *A61F 2210/0004* (2013.01); *A61F 2220/0016* (2013.01); *A61F 2220/0033* (2013.01); *A61F 2220/0075* (2013.01); *A61F 2230/0013* (2013.01); *A61F 2230/0054* (2013.01)

(56) References Cited

U.S. PATENT DOCUMENTS

| | | | |
|---|---|---|---|
| 6,322,590 B1 * | 11/2001 | Sillers | A61F 2/186 606/199 |
| 6,978,781 B1 | 12/2005 | Jordan | |
| 7,055,523 B1 | 6/2006 | Brown | |
| 7,114,495 B2 | 10/2006 | Lockwood, Jr. | |
| 7,972,379 B2 * | 7/2011 | Jung | A61F 2/186 623/10 |
| 8,216,311 B2 * | 7/2012 | Kang | A61F 11/20 606/204.45 |
| 8,480,737 B2 * | 7/2013 | Hristov | A61F 2/186 623/10 |
| 8,821,575 B2 | 9/2014 | Van Der Burg et al. | |
| D723,998 S * | 3/2015 | Hansen | D8/349 |
| 10,149,753 B2 * | 12/2018 | Chen | A61F 2/186 |
| 10,835,640 B2 * | 11/2020 | Stiefel | A61F 2/186 |
| 11,458,012 B2 * | 10/2022 | Zopf | A61L 27/18 |
| 11,564,792 B2 * | 1/2023 | Zopf | A61F 2/18 |
| 11,751,895 B2 * | 9/2023 | Yoon | A61B 17/32002 606/170 |
| 2004/0243157 A1 * | 12/2004 | Connor | A61M 3/0283 606/159 |
| 2007/0270899 A1 * | 11/2007 | aWengen | A61F 2/186 606/199 |
| 2011/0125091 A1 * | 5/2011 | Abbate | A61M 31/00 606/199 |
| 2012/0078367 A1 * | 3/2012 | Hristov | A61F 2/186 623/10 |
| 2012/0215307 A1 | 8/2012 | Chen et al. | |
| 2014/0039619 A1 | 2/2014 | Medizintechnik | |
| 2015/0148902 A1 * | 5/2015 | Komrit | A61F 2/0059 83/13 |
| 2015/0230917 A1 | 8/2015 | Ethicon | |
| 2016/0058556 A1 * | 3/2016 | Rosenthal | A61F 2/186 623/10 |
| 2017/0079777 A1 * | 3/2017 | Chen | A61F 2/186 |
| 2017/0143532 A1 * | 5/2017 | Gonzales | A61B 17/064 |
| 2019/0247183 A1 * | 8/2019 | Ahn | A61L 27/58 |
| 2020/0054446 A1 * | 2/2020 | Rosenthal | A61B 17/3468 |
| 2020/0078194 A1 * | 3/2020 | Feezor | A61F 2/186 |
| 2020/0155304 A1 * | 5/2020 | Nolens | A61L 27/56 |
| 2023/0149156 A1 * | 5/2023 | Rosenthal | A61L 27/58 623/10 |

OTHER PUBLICATIONS

PCT Written Opinion of the International Search Authority for PCT/US2017/059983, Applicant: The Regents of the University of California, Form PCT/ISA/237, dated Aug. 31, 2008 (8 pages).

\* cited by examiner

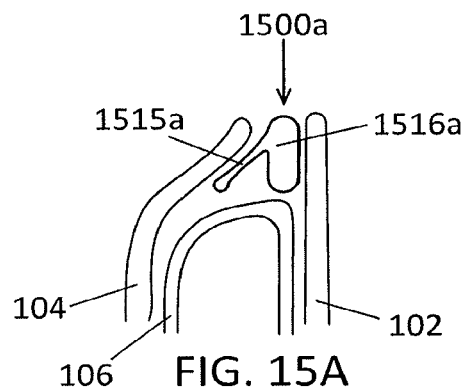
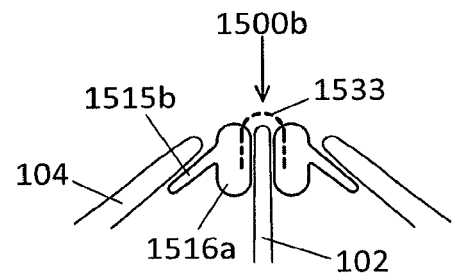
FIG. 15A          FIG. 15B
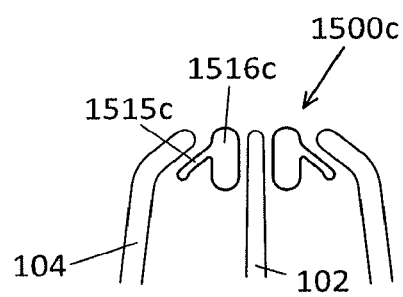
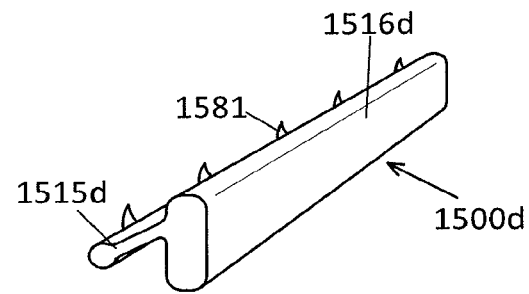
FIG. 15C          FIG. 15D
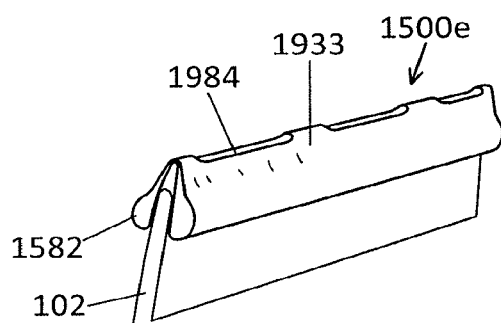
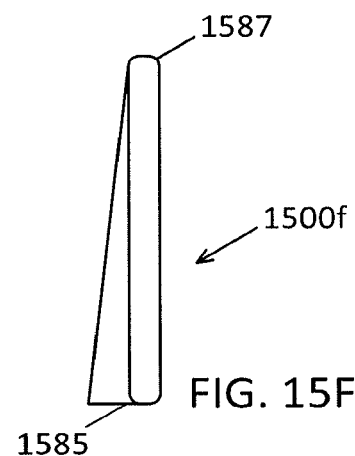
FIG. 15E          FIG. 15F
FIG. 15G

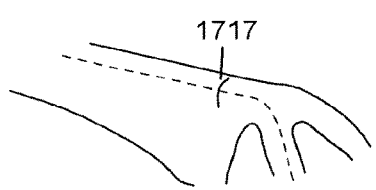
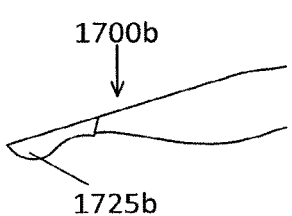
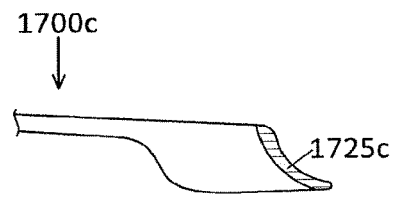
FIG. 17A     FIG. 17B     FIG. 17C
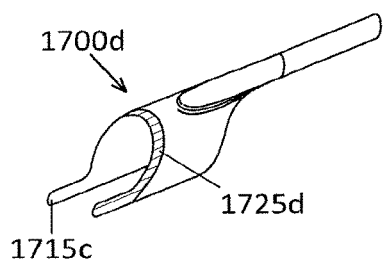
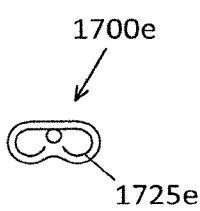
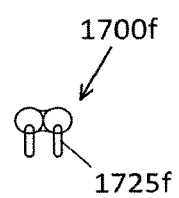
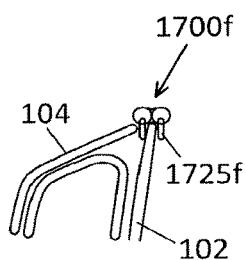
FIG. 17D    FIG. 17E    FIG. 17F    FIG. 17G
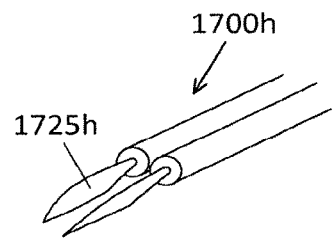
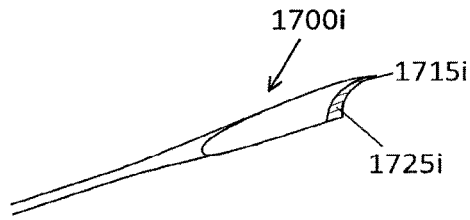
FIG. 17H                FIG. 17I
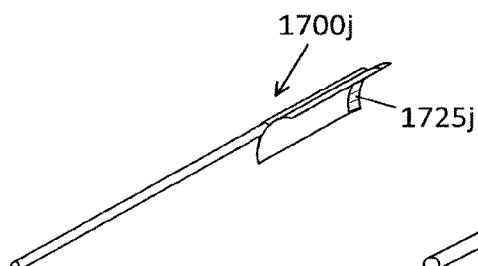
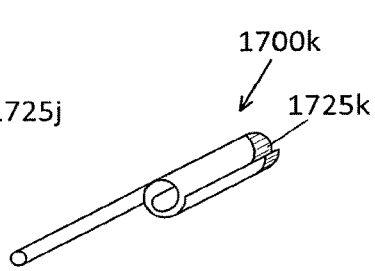
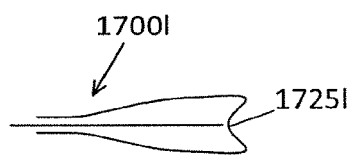
FIG. 17J     FIG. 17K     FIG. 17L

MINIMALLY INVASIVE NASAL IMPLANTS AND SYSTEMS AND METHODS

CROSS REFERENCE TO RELATED APPLICATIONS

This application is a continuation of U.S. application Ser. No. 16/346,048, filed Apr. 29, 2019, which is a national phase of International Application No. PCT/US17/59983, filed Nov. 3, 2017, which claims priority to U.S. Provisional Application No. 62/417,055, filed Nov. 3, 2016, the entirety of which are incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates generally to nasal implants and methods for delivering nasal implants in a minimally invasive procedure.

BACKGROUND

The internal nasal valve is the narrowest point in the nasal airway and is the point that often limits inspiration flow. A large percentage of inspiratory resistance is attributable to internal nasal valve function or malfunction. Collapse of one or both nasal valves is a common cause of nasal airway obstruction. Narrowness of the nasal valve may lead to difficulty in respiration and snoring as well as other breathing related disorders, such as sleep apnea. Nasal valve collapse can be a consequence of previous surgery, trauma, aging, or primary weakness of the upper or lower lateral cartilage and is often symptomatic and debilitating.

Surgery to strengthen the nasal valve has been shown to significantly improve quality of life for treated patients. The most common procedures for treating nasal valve collapse are alar batten grafting and spreader grafting. Additional procedures include surgically implanting dilators or using external dilators.

During the batten grafting procedure, a patient's cartilage is harvested from any one of a number of locations, such as the nasal septum or the ear. The cartilage is sculpted to an appropriate size and shaped and beveled on the edges for improved cosmetics. The batten graft is placed in the desired location of the nasal side-wall through either an external or endonasal approach. A pocket is formed overlying the cartilages of the nose with the pocket sized to receive the batten graft. The batten graft is then inserted into the pocket.

During the spreader grafting procedure, grafts are placed between the upper lateral cartilage and septum, typically in an open surgical approach that requires lifting a nasal skin flap. During the procedure, the attachment between the upper lateral cartilage and septum is severed, and a cartilage graft is placed between the two cartilages to alter the internal nasal angle or widen the nasal airway at the dorsum. Once in place, the spreader graft, upper lateral cartilage, and septum are sutured together, resulting in an increase in cross sectional area at the valve.

Dilators are also used to strengthen the nasal valve. An example of a surgically implanted dilator is found in U.S. Pat. No. 6,106,541 to Hurbis dated Aug. 22, 2000. In the '541 patent, the nasal dilator has a V-shape with an apex placed over the bridge of the nose to support the nasal tissue at the area of the internal valve. Other examples include U.S. Pat. No. 6,322,590 to Siller et al., dated Nov. 27, 2001. However, use of such dilators requires an open surgical technique for insertion.

External (non-implanted) nasal dilators which are placed temporarily, and are removed by the patient, are also available. Such external devices can be placed on the outside surface of the nose, such as the "Breathe Right" strips, U.S. Pat. No. 7,114,495. Other devices may be placed in the nasal cavity (but not implanted in the nose), such as those described in U.S. Pat. Nos. 7,055,523 and 6,978,781. However, such devices can be uncomfortable, unsightly, and require the patient to remove and replace the device on a periodic basis.

Therefore, there is a need for less invasive methods and devices for increasing the nasal valve cross sectional area or changing nasal valve angles.

SUMMARY OF THE DISCLOSURE

The present invention relates generally to nasal implants, nasal implant delivery tools, systems, and methods for delivering nasal implants.

In general, in one embodiment, a nasal implant includes a first longitudinal body adapted to engage with a septum or a septal cartilage of a patient, a second longitudinal body adapted to engage with a cartilage or an upper lateral cartilage of the patient, and a feature on at least one of the first and second longitudinal bodies adapted to connect the first and second longitudinal bodies. The nasal implant is sized to reside within a nasal tissue of the patient between a mucosa, the septum or septal cartilage, and the upper lateral cartilage to increase a cross-sectional area of a nasal airway.

This and other embodiments can include one or more of the following features. The nasal implant can further include a plurality of barbs along at least one of the first and second longitudinal bodies. The nasal implant can further include a curved portion connecting the first longitudinal body and the second longitudinal body. The nasal implant can further include a plurality of openings adapted to receive a suture. The nasal implant can further include a plurality of openings on one longitudinal body adapted to receive features extending from the second longitudinal body. The features extending from the longitudinal body can be barbs, hooks, slots, grooves, or projections. The nasal implant can further include a plurality of openings adapted to allow tissue ingrowth. The first longitudinal body, second longitudinal body, and any connection between the first longitudinal body and second longitudinal body can define a U-shape or V-shape.

In general, in one embodiment, a nasal implant includes a first longitudinal portion, a second longitudinal portion, and a bridge portion The first longitudinal portion has an inner surface adapted to engage with a first side of a septum or a septal cartilage of a patient and an outer surface adapted to engage with an upper lateral cartilage of the patient. The second longitudinal portion has an inner surface adapted to engage with a second side of the septum or the septal cartilage of the patient and an outer surface adapted to engage with the upper lateral cartilage of the patient. The bridge portion connects the first longitudinal portion and the second longitudinal portion adapted to engage with the septum or septal cartilage. The nasal implant is sized to reside within a nasal tissue of the patient between a mucosa, the septum or septal cartilage, and the upper lateral cartilage to increase a cross-sectional area of a nasal airway.

This and other embodiments can include one or more of the following features. The nasal implant can include a plurality of barbs along an outer surface of the first longitudinal surface and a plurality of barbs along an outer surface of the second longitudinal surface. The nasal implant can include a plurality of barbs along an outer surface of the first longitudinal surface and a plurality of openings along an outer surface of the second longitudinal surface adapted to engage with the plurality of barbs. The nasal implant can include a plurality of openings adapted to receive a suture. a plurality of openings adapted to allow tissue ingrowth. The bridge portion can be made out of a mesh material, textile, sheet, suture, or other open cell structure. The first longitudinal portion and/or second longitudinal portion can define a U-shape or V-shape.

In general, in one embodiment, a nasal implant includes a first longitudinal portion and a second longitudinal portion. The first longitudinal portion has an inner surface adapted to engage with a first side of a septum or a septal cartilage of a patient and an outer surface adapted to engage with an upper lateral cartilage of the patient. The second longitudinal portion has an inner surface adapted to engage with a second side of the septum or the septal cartilage of the patient and an outer surface adapted to engage with the upper lateral cartilage of the patient. The first longitudinal portion and the second longitudinal portion are adapted to engage with the septum or septal cartilage. The first longitudinal portion and the second longitudinal portion are adapted to be connected. The nasal implant is sized to reside within a nasal tissue of the patient between a mucosa, the septum or septal cartilage, and the upper lateral cartilage to increase a cross-sectional area of a nasal airway.

This and other embodiments can include one or more of the following features. The first longitudinal portion and the second longitudinal portion can include a plurality of openings adapted to receive sutures to connect the first longitudinal portion and the second longitudinal portion. The plurality of openings can be adapted to receive a suture in-situ. The nasal implant can include a plurality of openings adapted to allow tissue ingrowth. The nasal implant can be made out of a bioabsorbable material. The bioabsorbable material can be selected from the group consisting of: a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof. The nasal implant can be made out of a spun PTFE or poly-1-lactic acid (PLLA). the nasal implant is made out of a non-bioabsorbable material. The non-bioabsorbable material is selected from the group consisting of: ethylene vinyl acetate (EVA), poly(meth)acrylic acid, polyamides, silicone-based polymers and copolymers and mixtures thereof. Increasing the cross-sectional area of the nasal airway can include increasing a width of a nasal dorsum.

In general, in one embodiment, a dissection tool includes a proximal handle portion and a distal guide portion extending longitudinally from the proximal handle portion. The distal guide portion has a complementary structure to a portion of a septum/septal cartilage of a nasal tissue. The distal guide portion includes a cutting edge adapted to separate cartilage or tissue of a nasal anatomy from a first side of the septum and a second side of the septum.

This and other embodiments can include one or more of the following features. The distal guide portion can have a U-shaped cross sectional shape. The dissection tool can have an energy source adapted to assist with separating cartilage or tissue. The energy source can include radiofrequency (RF), resistance heating, or ultrasound. The energy source can be adapted to provide energy to the cutting edge. The dissection tool can further include a nasal implant compartment adapted to hold at least a portion of any of the nasal implants described herein. The cutting edge can have a curved shape. The cutting edge can be retractable from a retracted position within an internal portion of the distal guide portion and an advanced position extending from the internal portion of the distal guide portion. The dissection tool can include an atraumatic or rounded distal tip on the distal guide portion. The complementary structure of the distal guide portion can include a first projection, a second projection, and a bridge portion between the first projection and the second projection. The first projection can be adapted to slide along a first side of the septum/septal cartilage, and the second projection can be adapted to slide along a second side of the septum/septal cartilage. The cutting edge can be disposed between the first projection and the second projection. The dissection tool can be configured for a minimally invasive procedure.

In general, in one embodiment, a method of increasing a cross-sectional area of a nasal airway of a patient's nose includes: (1) inserting a tool having a surface with a cutting edge or a tissue separating edge into tissue of the nose; (2) advancing the tool and the surface to cut or separate a first portion of a nasal tissue on a first side of a septum and a second portion of the nasal tissue on a second side of the septum that opposes the first side of the septum; (3) placing a first implant or a first implant portion of a nasal implant within the patient's nose adjacent to the first portion of the nasal tissue on the first side of the septum; and (3) placing a second implant or a second implant portion of the nasal implant within the patient's nose adjacent to the second portion of the septal cartilage on the second side of the septum.

This and other embodiments can include one or more of the following features. The tool can include the surface with the cutting edge, and advancing the tool can include advancing the cutting edge to cut the first portion of the nasal tissue on the first side of the septum and the second portion of the nasal tissue on the second side of the septum that opposes the first side of the septum. The tool can include the surface with the tissue separating edge, and advancing the tool can include advancing the tissue separating edge to separate the first portion of the nasal tissue on the first side of the septum and the second portion of the nasal tissue on the second side of the septum that opposes the first side of the septum. Increasing the cross-sectional area of the nasal airway can include increasing a width of a nasal dorsum. The first implant or the first implant portion of the nasal implant can include a polymer and the second implant or the second implant portion of the nasal implant can include a polymer. The first portion of the nasal tissue can include a junction of the septal cartilage and the upper lateral cartilage. The second portion of the nasal tissue can include the junction of the septal cartilage and the upper lateral cartilage. The method can further include inserting a delivery tool into the nasal tissue including the nasal implant after the advancing step and prior to the placing step. The dissection tool can carry at least a portion of the nasal implant, and the method can further include after advancing the dissection tool, ejecting the nasal implant to place the nasal implant within the nasal tissue. The method can further include, after placing the implant, securing the first implant or the first implant portion of the nasal implant relative to the second implant or the second implant portion. Securing the first implant or the first implant portion can include threading a suture between the first implant or the first implant portion of the nasal implant and the second implant or the second implant portion. The method can further include threading a suture between the first implant or the first implant portion of the nasal implant and the second implant or the second implant portion. The method can further include tightening the suture between the first implant or the first implant portion of the nasal implant and the second implant or the second implant portion to secure the first implant or the first implant portion of the nasal implant relative to the second implant or the second implant. The nasal implant can further include a bridge portion between the first implant portion of the nasal implant and the second implant portion. Placing the first implant or the first implant portion of the nasal implant can include contacting the nasal implant between and with the upper lateral cartilage, septal cartilage, and mucosa. Placing the second implant or the second implant portion of the nasal implant can include contacting the nasal implant between and with the upper lateral cartilage, septal cartilage, and mucosa. The method can further include advancing a retractable blade from within an interior of the dissection tool prior to advancing the dissection tool. The method can be used with any of the implants described herein. The method can include use of any dissection tool described herein.

In general, in one embodiment, a system can include any of the nasal implants described herein combined with any of the dissection tools combined herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 11A shows the blade sheathed while FIG. 11B shows the blade extended.

FIGS. 15A-15G show various embodiments of nasal implants.

FIGS. 17A-L show various embodiments of dissection tools.

DETAILED DESCRIPTION

Figure 1:
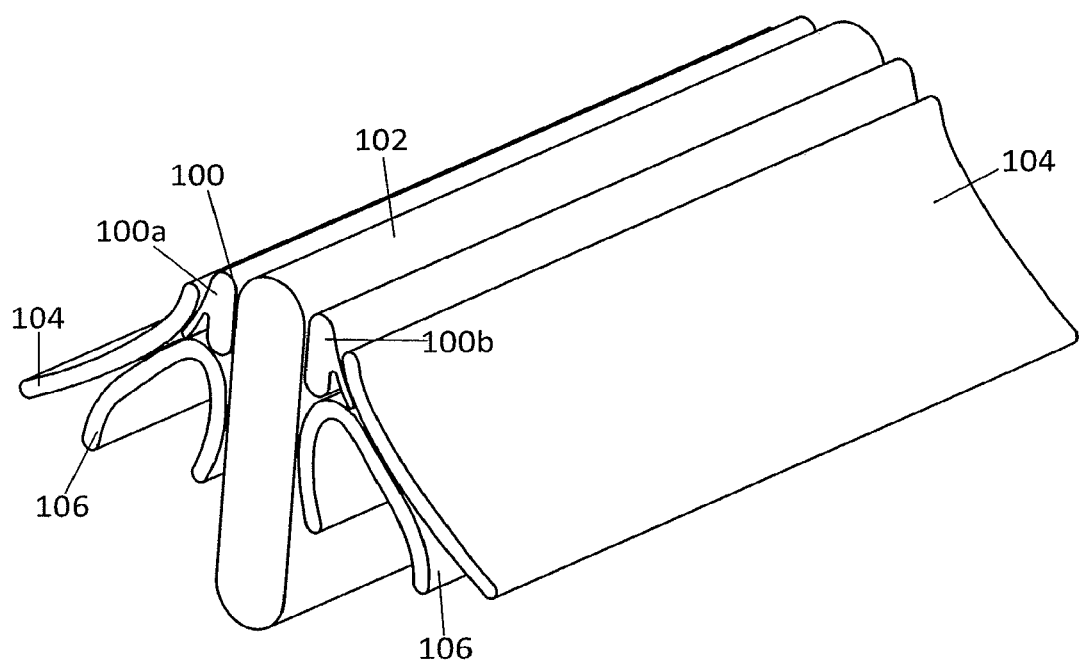
FIG. 1 shows a portion of a nasal anatomy with a nasal implant.

Nasal implants, systems for delivering nasal implants, tools for preparing nasal anatomy for the delivery of nasal implants, and methods of delivering nasal implants are described herein.

The nasal implant can be delivered to the nasal tissue of the patient in a minimally invasive manner. The use of minimally invasive techniques can improve patient recovery and decrease the likelihood of scarring and/or promote preferential scarring. The nasal implant can be used to change the anatomy of the nose, provide support for portions of the anatomy, or change the shape of the anatomy of the nose for the purposes of improving function or altering cosmetics. In one example, the nasal implant can create additional space at the connection between the upper lateral cartilage and the septum to increase the width of the airway at the nasal valve. Use of the nasal implant can advantageously prevent undesirable cosmetic changes that can result from more invasive surgical procedures and/or can better control desirable cosmetic changes. The nasal implant can be placed on one or both sides of the septum to provide support to the nasal tissue. Nasal implants on opposing sides of the septal cartilage can be optionally connected or tied together with a suture. In some embodiments, a single nasal implant can be used with portions that extend along each side of the septal cartilage along with a bridge portion that connects the two portions of the implant.

Further, methods are provided herein for increasing a cross-sectional area of a nasal airway of a patient's nose. The methods described herein can include delivering any of the nasal implants described herein. The methods can include delivering a nasal implant in a minimally invasive manner. For example, the nasal implant can be placed in a minimally invasive procedure without the need to make an incision in the columella. The nasal implants can be used to increase a width of the nasal dorsum. The methods can include inserting a tool having a surface with a cutting edge or a tissue separating edge into tissue of the nose, advancing the tool and the surface to cut or separate a first portion of a nasal tissue on a first side of a septum and a second portion of the nasal tissue on a second side of the septum that opposes the first side of the septum, followed by placing a first implant or a first implant portion of a nasal implant within the patient's nose adjacent to the first portion of the nasal tissue on the first side of the septum, and placing a second implant or a second implant portion of the nasal implant within the patient's nose adjacent to the second portion of the septal cartilage on the second side of the septum. The first portion of the nasal tissue and the second portion can include the septal cartilage and/or the upper lateral cartilage. Examples of the first portion and second portion of the nasal tissue include a junction of the septal cartilage and the upper lateral cartilage. When the tool includes the surface with the cutting edge, advancing the tool can include advancing the cutting edge to cut the first portion of the nasal tissue on the first side of the septum and the second portion of the nasal tissue on the second side of the septum that opposes the first side of the septum. The method can alternatively employ a separating tool used to separate tissue, rather than cutting it. For example, when the tool includes the surface with the tissue separating edge, advancing the tool can include advancing the tissue separating edge to separate the first portion of the nasal tissue on the first side of the septum and the second portion of the nasal tissue on the second side of the septum that opposes the first side of the septum. In some embodiments, the first implant or the first implant portion of the nasal implant comprises a polymer and the second implant or the second implant portion of the nasal implant comprises a polymer. The nasal implants need not be made out of a biological material, such as harvested cartilage.

In some embodiments, a delivery tool may be employed to place the implant at the desired location after cutting or separating the nasal tissue, such as the septal cartilage and/or the upper lateral cartilage. In some embodiments, no delivery tool is used, and the implant can be placed manually after the nasal tissue has been cut or separated to prepare for receiving the implant.

In some embodiments, the dissection tool can act as a delivery tool and can carry all or a portion of the nasal implant and then deploy the nasal implant within the nasal tissue. For example, the dissection tool can eject the nasal implant to place the nasal implant within the nasal tissue. In some embodiments, the dissection tool can include a retractable blade. For example, the methods can include advancing a retractable blade from within an interior of the dissection tool prior to advancing the dissection tool to cut the nasal tissue.

In some embodiments, delivering the implant can include using a suture to tie portions of the implant together and/or suture a portion of the implant to a portion of the nasal anatomy. The nasal implant can include openings that can be used to thread a suture. The suture can be threaded ex-vivo/ex-situ or in-vivo/in-situ and tightened after the implant is in the proper position in the nose engaged with the septal and/or lateral cartilages.

The nasal implant or portions of the nasal implant can be configured to be placed between and in contact with the upper lateral cartilage, septal cartilage, and mucosa.

Nasal implants are disclosed herein. The nasal implants can include a first longitudinal body adapted to engage with a septum or a septal cartilage of a patient, a second longitudinal body adapted to engage with a cartilage or an upper lateral cartilage of the patient, and a feature on at least one of the first and second longitudinal bodies adapted to connect the first and second longitudinal bodies. The nasal implant can be sized to reside within the nasal tissue of the patient between a mucosa, the septum or septal cartilage, and the upper lateral cartilage to increase a cross-sectional area of a nasal airway. In some embodiments, the nasal implants can include a plurality of barbs along the first and/or second longitudinal body to improve engagement with the adjacent nasal tissue. In some embodiments, the nasal implant can include a curved portion connecting the first longitudinal body and the second longitudinal body. In some embodiments, the nasal implants described herein can include a plurality of openings adapted to receive a suture. In some embodiments, the nasal implants may include both barbs and openings intended to improve engagement with adjacent nasal tissue and enable engagement between opposing implants. In some embodiments, the nasal implant can include a plurality of openings on one longitudinal body adapted to receive features extending from the second longitudinal body. Examples of the features extending from the longitudinal body are barbs, hooks, slots, grooves, or projections. The features extending from the longitudinal body can engage with openings on another longitudinal body and/or cartilage. Combinations of the different features can be used in some cases. In some embodiments, the nasal implants can include a plurality of openings adapted to allow tissue ingrowth. In some embodiments, the first longitudinal body, second longitudinal body, and any connection between the first longitudinal body and second longitudinal body define a U-shape or V-shape.

Nasal implants that include a bridge structure adapted to overlay a portion of the septal cartilage are also described herein. Such nasal implants can include a first longitudinal portion having an inner surface adapted to engage with a first side of a septum or a septal cartilage of a patient and an outer surface adapted to engage with an upper lateral cartilage of the patient, a second longitudinal portion having an inner surface adapted to engage with a second side of the septum or the septal cartilage of the patient and an outer surface adapted to engage with the upper lateral cartilage of the patient, and a bridge portion connecting the first longitudinal portion and the second longitudinal portion adapted to engage with the septum or septal cartilage. The nasal implant can be sized to reside within a nasal tissue of the patient between a mucosa, the septum or septal cartilage, and the upper lateral cartilage to increase a cross-sectional area of a nasal airway. The bridge portion can be made out of a mesh material, textile, sheet, suture, or other open cell structure. In some cases the bridge portion can be made out of a solid or continuous flexible material or both. The first longitudinal portion and/or second longitudinal portion can define a U-shape or V-shape. The nasal implant can include a plurality of barbs along an outer surface of the first longitudinal surface and a plurality of barbs along an outer surface of the second longitudinal surface. The nasal implant can include a plurality of openings adapted to receive a suture or opposing implant barbs. In some embodiments, the nasal implant can include a plurality of barbs along an outer surface of the first longitudinal surface and a plurality of openings along an outer surface of the second longitudinal surface adapted to engage with the plurality of barbs. The nasal implant can include a plurality of openings adapted to allow tissue ingrowth.

Additional examples of nasal implants are also described herein. The nasal implant can include a first longitudinal portion having an inner surface adapted to engage with a first side of a septum or a septal cartilage of a patient and an outer surface adapted to engage with an upper lateral cartilage of the patient and a second longitudinal portion having an inner surface adapted to engage with a second side of the septum or the septal cartilage of the patient and an outer surface adapted to engage with the upper lateral cartilage of the patient. The first longitudinal portion and the second longitudinal portion can be adapted to engage with the septum or septal cartilage. The first longitudinal portion and the second longitudinal portion can be adapted to be connected by sutures or other connecting structures. The nasal implant can be sized to reside within a nasal tissue of the patient between a mucosa, the septum or septal cartilage, and the upper lateral cartilage to increase a cross-sectional area of a nasal airway. In some embodiments, the first longitudinal portion and the second longitudinal portion can include a plurality of openings adapted to receive sutures to connect the first longitudinal portion and the second longitudinal portion. The plurality of openings can be adapted to receive a suture in-situ. The nasal implant can further include a plurality of openings adapted to allow tissue ingrowth.

The nasal implants described herein can be made out of a variety of different materials. The nasal implants described herein can be made out of a bioabsorbable material, such as a polymer designed to degrade over a predetermined timeframe. For example, the bioabsorbable material can be polylactic acid (PLA), polyglycolide (PGA), polycaprolactone (PCL), or polydioxanone (PDO). Further, the bioabsorbable material can be in various forms such as perforated sheets, meshes or textiles composed of individual fibers. In some cases, a non-bioabsorbable material can be used. In some cases, the nasal implant can include both bioabsorbable materials and non-bioabsorbable materials. In some embodiments, the nasal implants can be made out of a spun material, such as spun polytetrafluoroethylene (PTFB) or poly-1-lactic acid (PLLA).

An implant as described herein may be made of any biocompatible material that provides the desired support and shaping properties of the implant. The implant may be partially or wholly made from a non-biodegradable material as known in the art such as any polymer, metal, or shape memory material. An implant may be made from organic and/or inorganic materials. The material of the implant may be solid (e.g. titanium, nitinol, or Gore-tex) or braided or woven from a single material (such as titanium, or Polyethylene Terephthalate, or a combination of materials). If braided or woven, the implant material may have pores which allow ingrowth of tissue after implantation. Representative synthetic polymers for use in the implants described herein include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyacrylamides, polyorthoesters, polyphe azenes, polysiloxanes, polyurethanes, polyvinyl alcohols, polyvinyl esters, polyvinyl ethers, polyvinyl halides, polyvinylpyrrolidone, poly(ether ketone)s, silicone-based polymers and blends and copolymers of the above. Specific examples of these broad classes of polymers include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyurethane, poly(lactic acid), poly(butyric acid), poly(valeric acid), poly[lactide-co-glycolide], poly(fumaric acid), poly(maleic acid), copolymers of poly (caprolactone) or poly (lactic acid) with polyethylene glycol and blends thereof.

In embodiments wherein the nasal implant described herein is biodegradable, the implant may be made from a poly(lactide); a poly(glycolide); a poly(lactide-co-glycolide); a poly(lactic acid); a poly(glycolic acid); a poly (lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly (oxyethylene)/poly(oxypropylene) copolymer, or a blend or copolymer thereof. In some examples, an implant includes poly-L-lactic acid (PLLA) or poly-D-lactic acid (PDLA) or both. In some examples, an implant is 90:10, 80:20, 70:30, 60:40, 50:50 PLLA/PDLA copolymer or is in between any of these values. In some examples, an implant is 70:30, +/−10% PLLA/PDLA copolymer.

In some embodiments, a polymer used for the implants described herein may be non-biodegradable. Examples of non-biodegradable polymers that may be used include ethylene vinyl acetate (EVA), poly(meth)acrylic acid, polyamides, silicone-based polymers and copolymers and mixtures thereof.

Cutting or separating tools are also described herein that can be used to cut or separate tissue to provide access to the target anatomy locations within the nasal tissue. The dissection tools can include a proximal handle portion and a distal guide portion extending longitudinally from the proximal handle portion. The distal guide portion can have a complementary structure to a portion of a septum/septal cartilage of a nasal tissue. The distal guide portion can include a cutting edge adapted to cut a cartilage of a nasal anatomy on a first side of the septum and a second side of the septum. The distal guide portion can have a V-shaped or U-shaped cross sectional shape. The dissection tool can include a cutting edge that has a curved shape. In some embodiments, the tool can include an energy source adapted to assist with separating cartilage or tissue. Examples of the energy source include radiofrequency (RF), resistance heating, or ultrasound. The energy source can be adapted to provide energy to the cutting edge. In some embodiments, the dissection tool includes a retractable blade. For example, the cutting edge can be retractable to a retracted position within an internal portion of the distal guide portion from an advanced position extending from the internal portion of the distal guide portion. The dissection tools can include an atraumatic or rounded distal tip on the distal guide portion that can preferentially minimize the chances of the tool puncturing, piercing, or damaging selective adjunctive tissue structures (e.g. epidermis) when the tool is advanced. The complementary structure of the distal guide portion can include a first projection, a second projection, and a bridge portion between the first projection and the second projection. The first projection can be adapted to slide along a first side of the septum/septal cartilage and the second projection can be adapted to slide along a second side of the septum/septal cartilage. In some embodiments, the cutting edge is disposed between the first projection and the second projection. The dissection tool can also include a nasal implant compartment adapted to hold at least a portion of any of the nasal implants described herein.

Kits and systems are also described herein including any of the nasal implants and any of the dissection tools described herein. The kits and systems can also include a delivery tool adapted to deploy the implant within the targeted nasal tissue.

FIG. 1 is a schematic illustration of a portion of a nasal anatomy with nasal implants 100*a,b* in accordance with some embodiments. FIG. 1 shows the nasal anatomy, including the cartilage 104 (e.g., such as the upper lateral cartilage), septum/septal cartilage 102, and mucosa 106. Further, FIG. 1 shows a nasal implant 100*a,b* on both sides of the septum 102. On a first side of the septum 102, the nasal implant 100*a* is positioned between the septum/septal cartilage 102, cartilage 104, the mucosa 106, and the skin overlying the nasal anatomy (not pictured). A nasal implant 100*b* is also on the second opposing side of the septum 102 and positioned between the septum/septal cartilage 102, cartilage 104, the mucosa 106, and the skin overlying the nasal anatomy (not pictured). The nasal implants 100*a,b* can modify the shape of the nose of the patient receiving the implants 100*a,b* and thereby increase the cross sectional area of the airway at the nasal valve.

FIG. 1 illustrates two separate nasal implants 100*a,b* on opposing sides of the septum 102, but the separate nasal implants 100*a,b* can optionally be connected by a bridge, sutures, or other flexible structure as described herein. In some embodiments, for example, sutures can be used to secure the nasal implant to the septum or other portion of the nasal anatomy and/or to secure the nasal implant on one side of the septum to the nasal implant on the opposing side of the septum. In some embodiments, a bridge or connecting structure can connect the nasal implants on opposing sides of the septum. The bridge or connecting structure can have a flexible configuration and be adapted to overlie and engage with the septum/septal cartilage. Further, in some embodiments, only a single implant (100*a* or 100*b*) is used. In some embodiments, each implant can have a circular or ovular cross-section. In other embodiments, each implant can have a rectangular cross-section.

Figure 2:
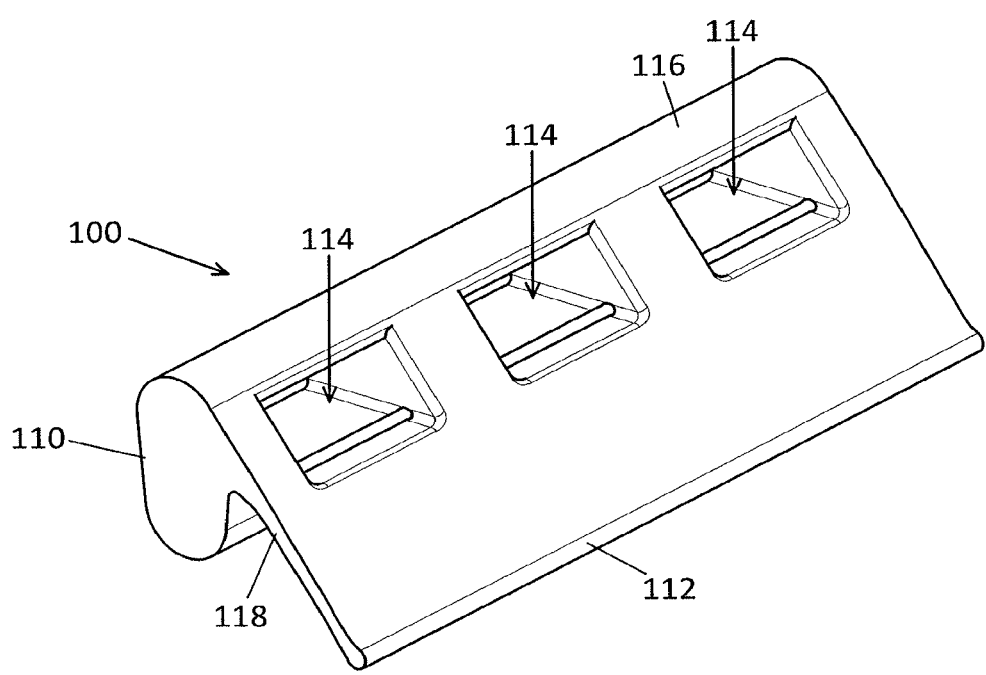
FIG. 2 shows an embodiment of a nasal implant.

FIG. 2 shows a single nasal implant 100 (which can be used as either implant 100*a* or 100*b* in FIG. 1). The implant 100 has an elongate shape with a winged cross-section. A first side 110 of the winged implant 100 has a generally flat surface that is shaped and sized to lie adjacent to the septum/septal cartilage 102 to change the cross-sectional airway of the pathway, such as increasing the width of the nasal dorsum. The second, opposite side 112 of the winged implant 100 has a flat angled surface that can be sized and shaped to engage with a portion of the cartilage 104 of the nose, as shown in FIG. 1. The nasal implant 100 includes a rounded surface portion 116 configured to be placed between the septum/septal cartilage engagement surface 110 while the second side 112 engages with the cartilage of the nose 104. The nasal implant 100 can also include a lower surface 118 adapted to engage with or accommodate the underlying nasal anatomy, such as the mucosa 106. Further, the nasal implant 100 can optionally include openings 114 that can be used with sutures and also facilitate tissue ingrowth. Further, the implant 100 can include optional modifications to the exterior surfaces to improve engagement with the nasal anatomy. For example, one or more of the exterior surfaces can have a roughened surface to improve engagement with the anatomy or one or more prongs, barbs, or other tissue engagement structures to improve engagement with the nasal anatomy.

Figure 8:
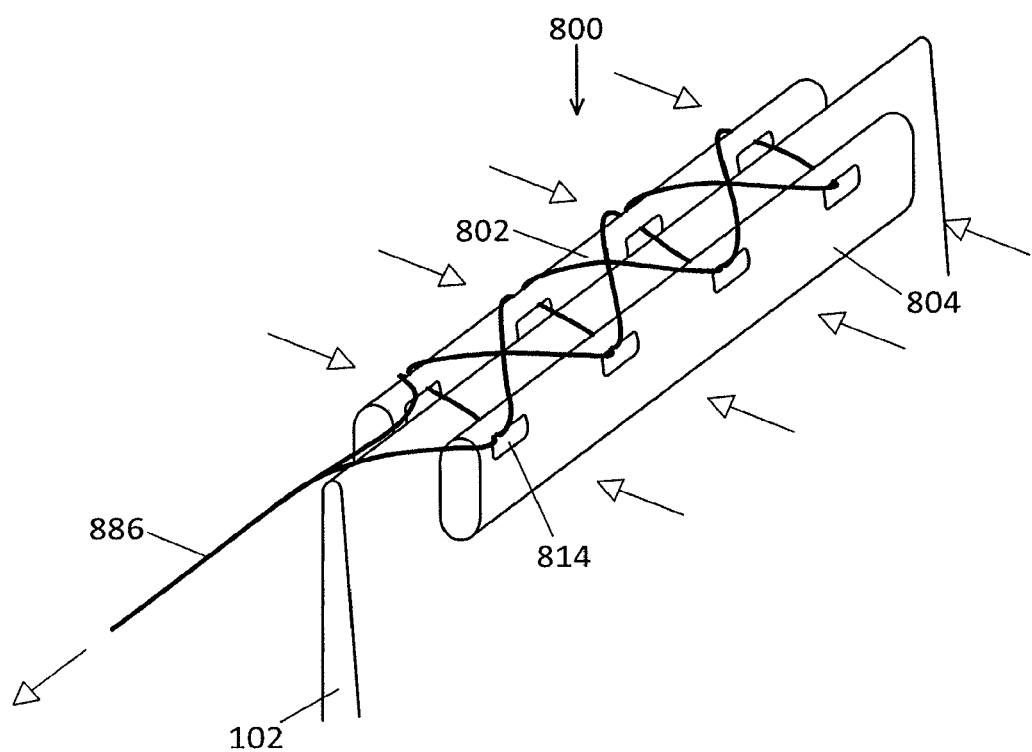
FIG. 8 shows an embodiment of a nasal implant engaged with a nasal anatomy.

FIG. 8 illustrates another exemplary nasal implant 800 engaged with a nasal anatomy (e.g., over the septum 102). The nasal implant 800 includes a first section 802 and a second section 804 connected via a suture 886. The suture 886 can pass through multiple openings 814 in the first section 802 and in the second section 804 (e.g., in a parallel and crisscross pattern). During implantation, the suture 886 can be pulled proximally to pull the first section 802 and second section 804 towards one another and tighten the implant 800 around the septum 102. The suture 806 can thus be tightened in situ. In other embodiments, the nasal implant 800 can be introduced to the nasal anatomy with the first section 802 and second section 804 connected with a preset spacing. Once the nasal implant 800 is in place with the preset spacing, the tension to the suture 806 can be adjusted to achieve the desired final position.

Figure 9:
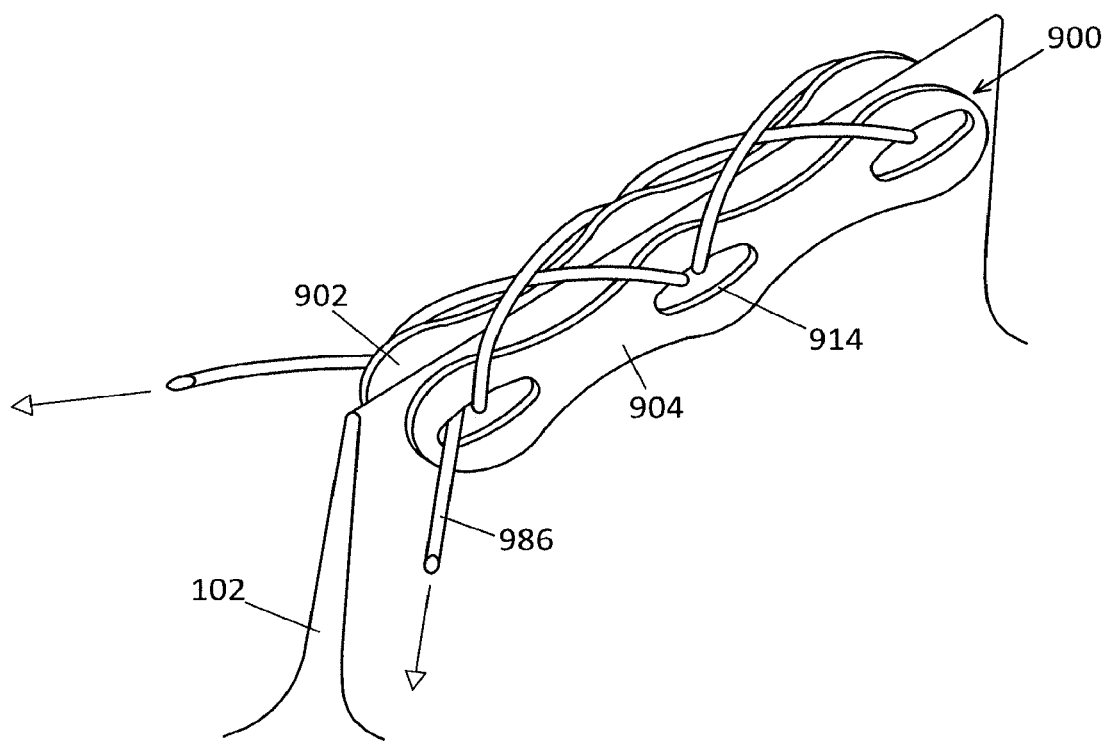
FIG. 9 shows an embodiment of a nasal implant engaged with a nasal anatomy.

FIG. 9 illustrates a nasal implant 900 that is similar to nasal implant 800 except that the suture 986 is threaded in a simple crisscross pattern. The nasal implant 900 includes a first section 902 and a second section 904 with a plurality of openings 914 threaded by a suture 986. The suture 986 can be cinched to pull the first section 902 and second section 904 into position and to engage with the septum 102.

Figure 14A:
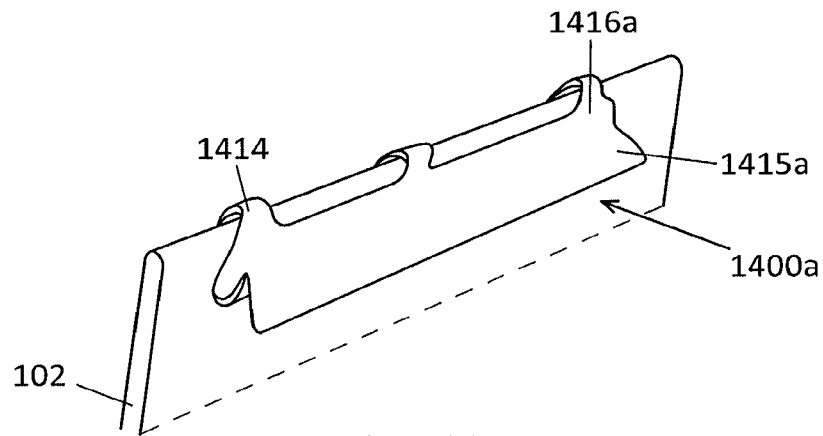
FIG. 14A shows a winged nasal implant engaged with the nasal anatomy.
Figure 14B:
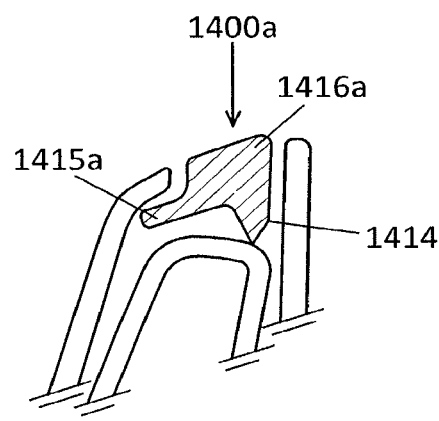
FIG. 14B is a cross-section of FIG. 14A.
Figure 14C:
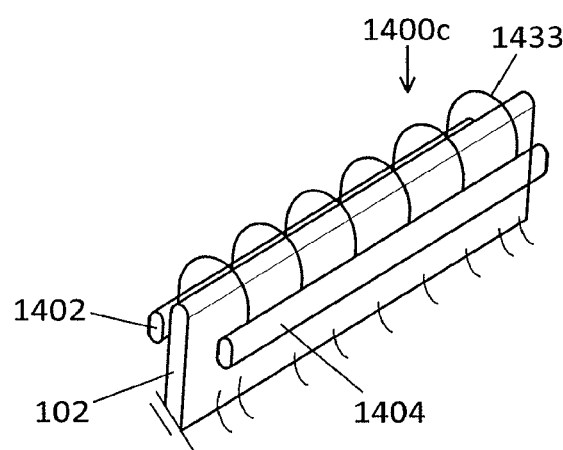
FIG. 14C shows another embodiment of a nasal implant engaged with the nasal anatomy.

FIGS. 14A-14C illustrate examples of nasal implants in accordance with some embodiments. As shown in FIGS. 14A-B, the nasal implant 1400*a* can include a winged configuration (e.g., have a central body 1416*a* and a wing 1415*a* extending therefrom). Further, the implant 1400*a* can include barbs 1414 configured to curve around to engage with the top of the septum 102. Referring to FIG. 14C, the nasal implant 1400*c* can include first and second portions 1402, 1404 configured to extend on either side of the septum 102 and a flexible bridge 1433 extending therebetween. In some cases, the flexible bridge 1433 can be made out of discrete filaments, sutures, or wires. In other embodiments, the flexible bridge 1433 can be woven. In some embodiments, the bridge 1433 can be made of a biodegradable or bioabsorbable material.

FIGS. 15A-15G illustrate different nasal implant configurations in accordance with some embodiments. For example, as shown in FIGS. 15A-15D, the implants 1500*a-d* all have a winged cross-section, where the wing(s) 1515*a-d* extend laterally away from the central body 1516*a-d*. The wings 1515*a-d* can be configured to engages with a portion of the lateral upper cartilage 104 while the central bodies 1516*a-d* can be configured to engage with the septal cartilage 102. The wings 1515a-d can be configured to extend away from the central body 1516a-d (e.g., 60-90 degrees away) to further open the nasal passage. In some embodiments, the implants 1500a-d each be implanted on both sides of the septum 102 and connected with a bridge 1533. Referring to FIG. 15D, in some embodiments, a plurality of barbs 1581 can be positioned on the wing 1515d or central body 1516d (e.g., on the top surfaces thereof) to further engage with the cartilage. Referring to FIG. 15E, in some embodiments, the nasal implant 1500e can have a narrow profile with a bulbous bottom portion 1582 and a tapered thin bridge 1933. The bridge 1933 can include a plurality of openings 1984 therein configured to permit fluid flow and improve healing. Referring to FIGS. 15F-15G, in some embodiments, the implant 1500f can include a tapered axial profile. The thicker profile end 1585 of the nasal implant 1500f can be configured to engage with a portion of the septal cartilage 102 near the anterior portion of the nose and the thinner portion 1587 can be configured to be positioned at the distal/posterior/or cranial side of the implant.

Figure 16:
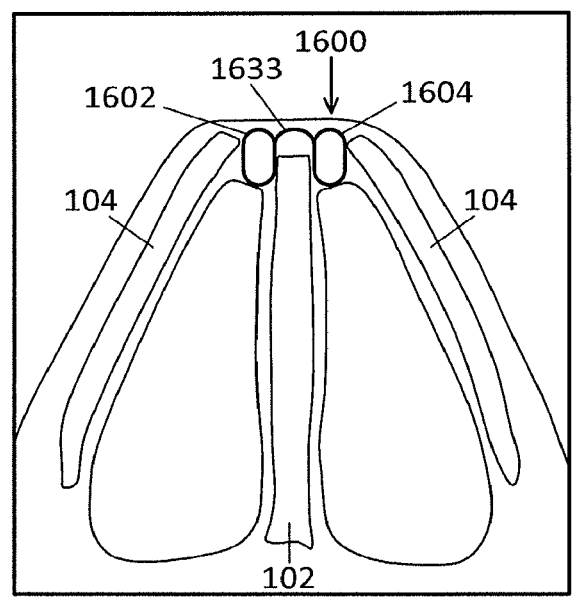
FIG. 16 shows an exemplary nasal implant engaged with the nasal anatomy.

FIG. 16 illustrates a nasal implant 1600 with a bridge 1633 extending between two portions 1602, 1604. The bridge 1633 can be made out of a variety of different materials. In some embodiments, the bridge 1633 can be made out of a bioabsorbable material, biodegradable material, non-woven material, and other biocompatible materials. In one example, the bridge 1633 can be made of a spun PTFE material. In another example, the bridge 1633 can be made of a spun poly L lactic acid (PLLA). The bridge 1633 can extend over the septum 102 while the portions 1602, 1604 can extend between the septum 102 and cartilage 104.

Figure 19A:
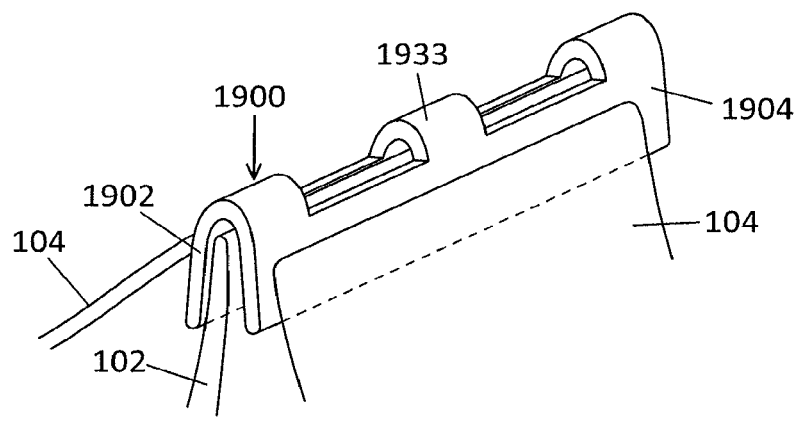
FIGS. 19A-19B show an embodiment of a nasal implant in the nasal anatomy.
Figure 19B:
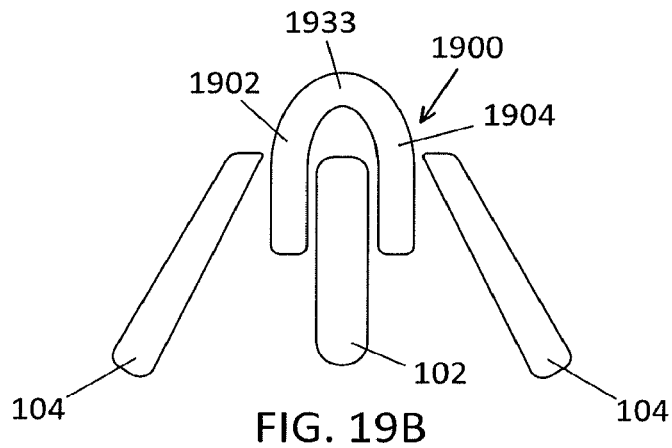
Figure 19C:
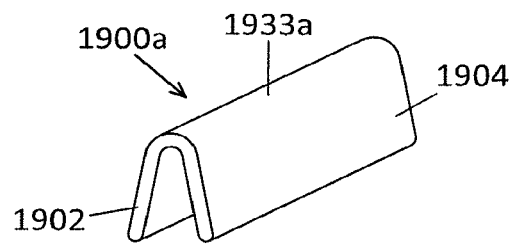
FIG. 19C shows another embodiment of a nasal implant.

FIGS. 19A-19C illustrate different exemplary embodiments of nasal implants. The nasal implant 1900 includes an integral construction for the portions 1902, 1904 engaged on either side of the septum 102. An arched bridge portion 1933 extends integrally between the portions 1902, 1904. The bridge portion 1933 can include discrete sections extending axially along the septum 102, e.g., three discrete sections as shown in FIG. 19A. The spaces between the discrete bridge portions can allow for fluid movement and to improve tissue healing. The implant 1900a of FIG. 19C is similar to implant 1900 except that the bridge portion 1933a is v-shaped and is solid along the longitudinal axis (i.e., does not include discrete sections).

Figure 3A:
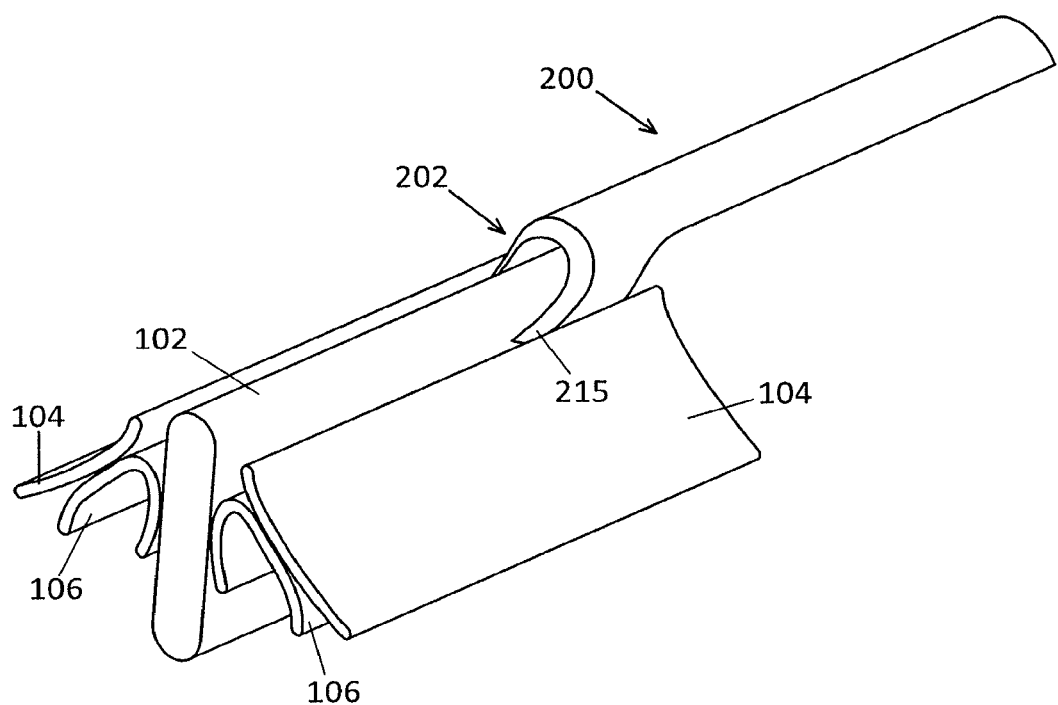
FIG. 3A shows an embodiment of a dissection tool that can be used before or during delivery of the nasal implants described herein.

In some embodiments, a dissection tool can be used to prepare for and/or deliver a nasal implant as described herein. For example, FIG. 3A shows an embodiment of a cutting or dissection tool 200 that can be used in methods to deliver a nasal implant. The dissection tool 200 can have a distal cutting edge 202 with a U-shaped cross section and a pointed bottom tip 215. The cutting edge 202 can be adapted to engage with the septum/septal cartilage 102 and cut the upper lateral cartilages 104 away from the septum 102 to make space for placing the nasal implant without damaging the mucosa 106.

Figure 3B:
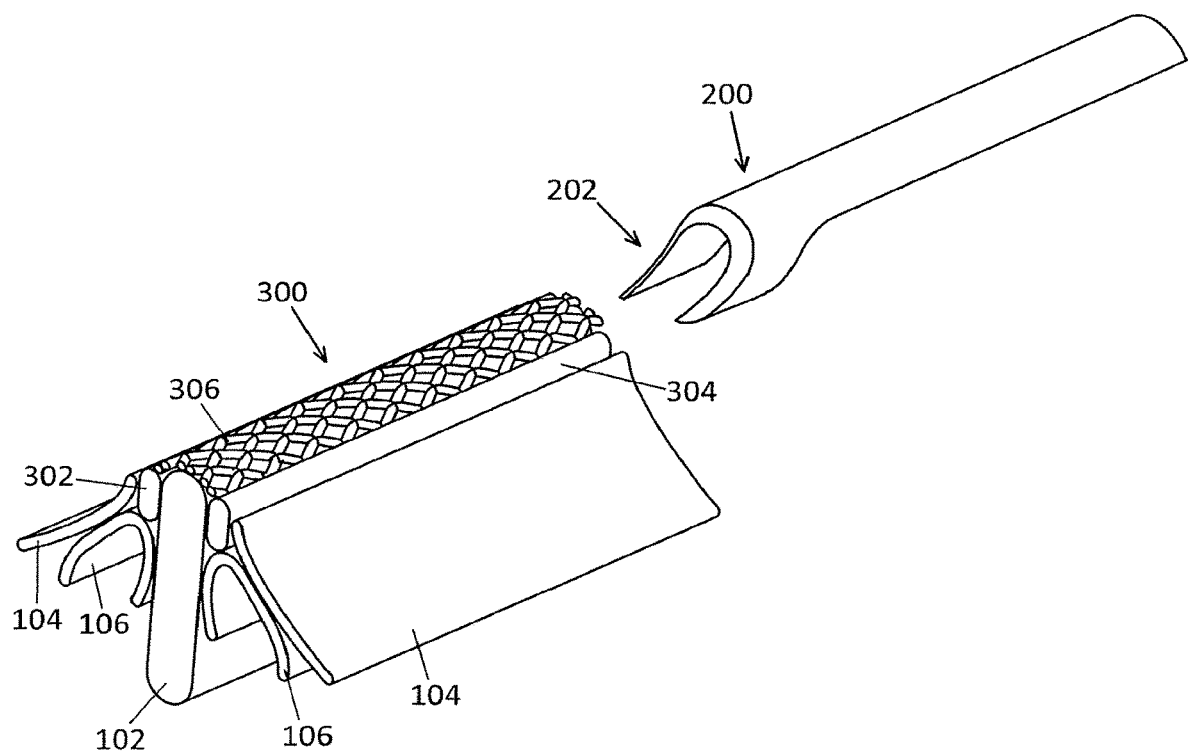
FIG. 3B shows a nasal implant engaged with the nasal anatomy and a dissection tool that can be used during delivery of the implant.

FIG. 3B shows a nasal implant 300 that can be delivered with the dissection tool 200. The nasal implant 300 includes first portion 302 adapted to engage with a first side of the septum/septal cartilage 102 (between the septum 102 and the cartilage 104), a second portion 304 adapted to engage with a second side of the septum/septal cartilage 102 (between the septum at the cartilage 104), and a bridge portion 306 adapted to connect the first portion 302 and the second portion 304. The dissection tool 200 can be used to cut the cartilage 104 away from the septum 102 to make space for the nasal implant 300.

Figure 4:
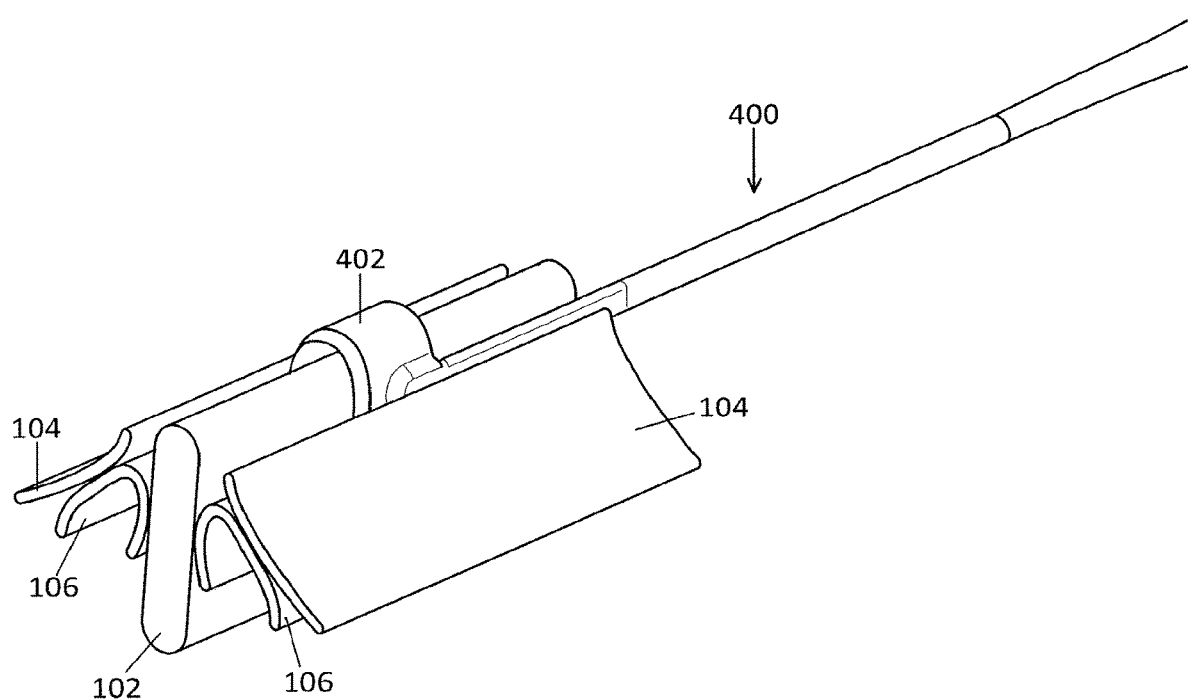
FIG. 4 shows an embodiment of a dissection tool in use in the nasal anatomy.

FIG. 4 shows another exemplary embodiment of a cutting or dissection tool 400 that can be used in methods to deliver the nasal implants described herein. The dissection tool 400 includes a distal cutting edge 402 with an offset curved cross-section that is adapted to slide along both sides of the septum/septal cartilage 102. The dissection tool 400 can be advanced such that the distal end 402 slides up along the septum/septal cartilage 102 and can cut the junction of the septal to upper lateral cartilage 104 to make room for the nasal implant.

In some embodiments, the dissection tools 200/400 can be used to deliver the nasal implant. In other embodiments, the tools 200/400 can be used in combination with a separate delivery tool.

Figure 5:
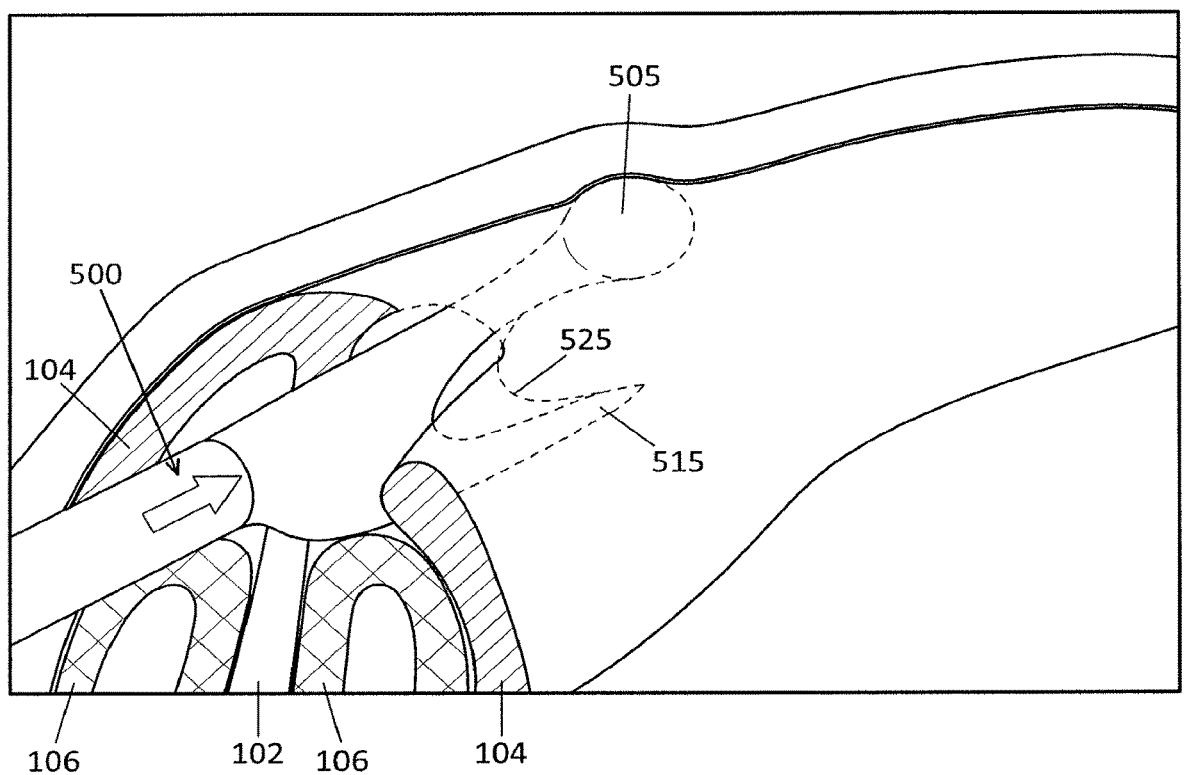
FIG. 5 shows an embodiment of a dissection tool engaged with the nasal anatomy.

FIG. 5 illustrates an embodiment of a dissection tool 500 engaged with a nasal anatomy. The dissection tool 500 can be used to cut the junction of the septum 102 to the upper lateral cartilage 104 and provide access to the desired nasal implant location in the nasal passage in a minimally invasive manner. The dissection tool 500 can have a distal end with an atraumatic tip 505 that can minimize the likelihood of piercing through the skin during use in the nasal passage. The dissection tool 500 can also include a scooped sharp cutting edge 525 and a pointed portion 515 for piercing cartilage if necessary. The edge 525 can further be configured to guide the tool 500 along interior surface of the junction of the septum 102 and the upper lateral cartilage (ULC) 104. The cutting edge 525 can extend between the pointed portion 515 and the atraumatic tip 505. The cutting edge 525 can be configured to cut through a portion of the nasal tissue to open up a space for the nasal implant, such as at the connection between the septum 102 and the upper lateral cartilage 104. The tool 500 can be advanced to cut open the space for the nasal implant and then be withdrawn. The implant can then be placed in the nasal passageway in a minimally invasive manner.

Figure 6A:
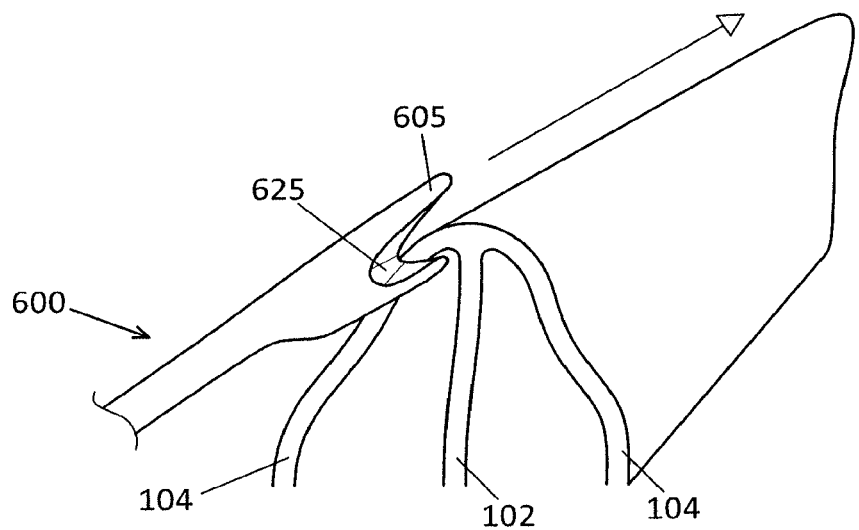
FIG. 6A shows an embodiment of a dissection tool engaged with a nasal anatomy.
Figure 6B:
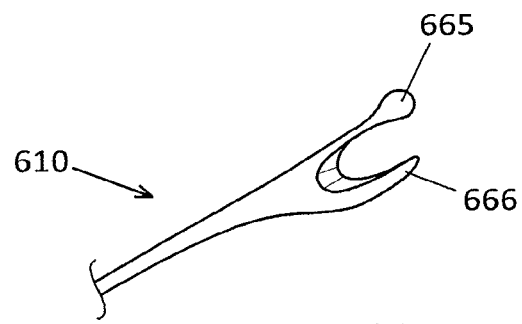
FIG. 6B shows another embodiment of a dissection tool.

FIG. 6A illustrates embodiments of a dissection tool 600 engaged with a nasal anatomy. The dissection tool 600 includes a scooped cutting blade 625 and a blunt or atraumatic tip 605. The cutting blade 625 can be advanced to cut a portion of the nasal anatomy between the septum 102 and cartilage 104 as illustrated. Further, the atraumatic tip 605 can minimize the chances of the tool 600 piercing the skin during use. FIG. 6B shows a dissection tool 610 that is similar to tool 600 and includes an atraumatic tip 665 and a sharp pointed tip 666, but does not include a scooped cutting edge.

Figure 7A:
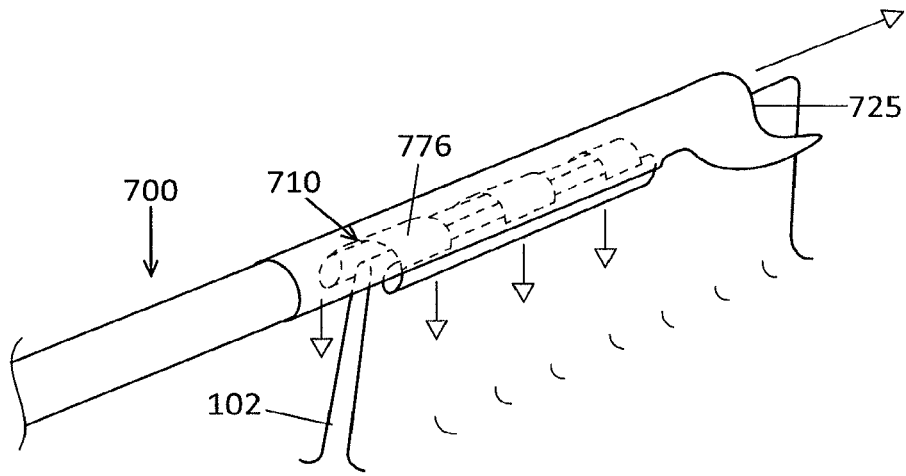
FIG. 7A shows a dissection tool that can be configured to deliver an implant to the nasal anatomy.
Figure 7B:
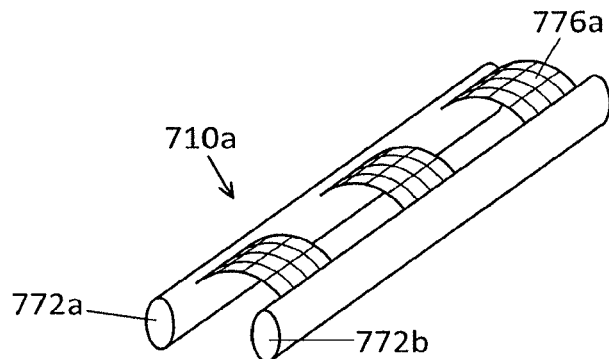
FIGS. 7B and 7C show embodiments of nasal implants.
Figure 7C:
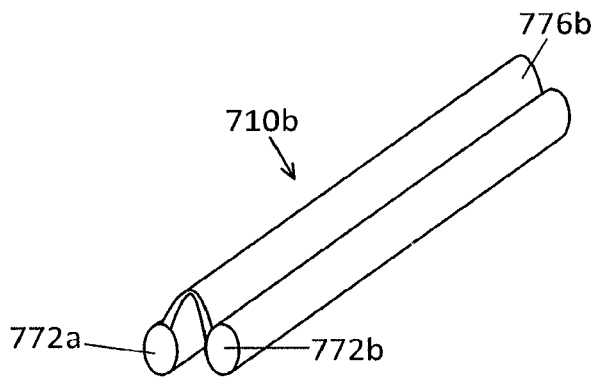

FIG. 7A illustrates a dissection tool 700 for delivering an implant 710 that includes a bridge 776 in accordance with some embodiments. The dissection tool 700 includes a distal cutting edge 735 and a hollow interior configured to contain and deliver the implant 710 over the septum 102. Further, the dissection tool 700 can cut a portion of the nasal anatomy (e.g., between the septum 102 and cartilage) as it is advanced. Once the portion of the nasal tissue is cut, then the implant 710 can be delivered to the target location. FIG. 7A shows the nasal implant 710 being placed over the septum 102. Referring to FIGS. 7B-7C, the nasal implant 710 (or 710a,b) that can be delivered with dissection tool 700 includes a first section 772a deployed on one side of the septum 102 and a second section 772b deployed on an opposing side of the septum 102 with a bridge structure (776a or 776b) spanning between the first section 772a and second section 772b. As shown in FIG. 7B, the implant 710 (here 710a) can include a mesh bridge 776a and/or can include a plurality of discrete bridge sections. As shown in FIG. 7C, the implant 710 (here 710b) can include a solid bridge 776b and/or the bridge can be made of a single piece.

Figure 10A:
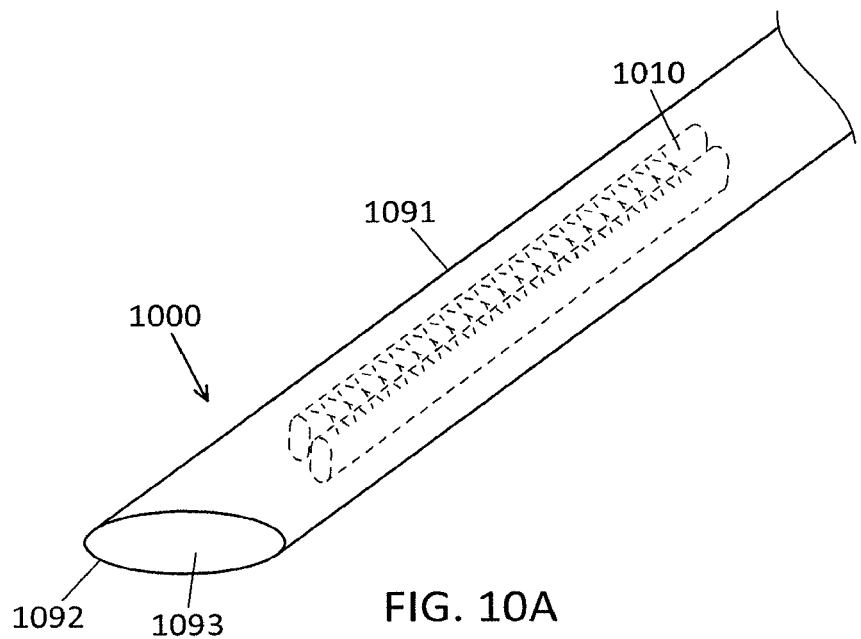
FIG. 10A shows a delivery tool carrying a nasal implant.
Figure 10B:
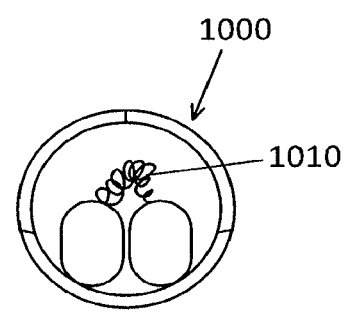
FIG. 10B is a cross-section of FIG. 10A.

FIGS. 10A-10B illustrate a delivery tool 1000 carrying a nasal implant 1010 in accordance with some embodiments. The delivery tool 1000 includes a hollow cannula 1091 with a pointed distal end 1092. The implant 1010 can fit within the hollow cannula 1091. In some embodiments, the implant 1010 can be in a compressed configuration within the cannula 1091 for delivery to the desired location and can then be expanded into the desired configuration. In some embodiments, the nasal implant 1010 can be ejected through the opening 1093 at the distal tip of the cannula 1091 in the desired position and orientation. The implant 1010 can be any implant described herein and can include sutures connecting the two portions (as shown in FIG. 10A) or a bridge, such as a mesh bridge connecting the two portions (as shown in FIG. 10B). Additionally, in some embodiments, the delivery tool 1000 can be configured to an deploy an implant only to one side of the septum and then, for example, to sequentially deploy the implant on the opposite side of the septum.

Figure 11A:
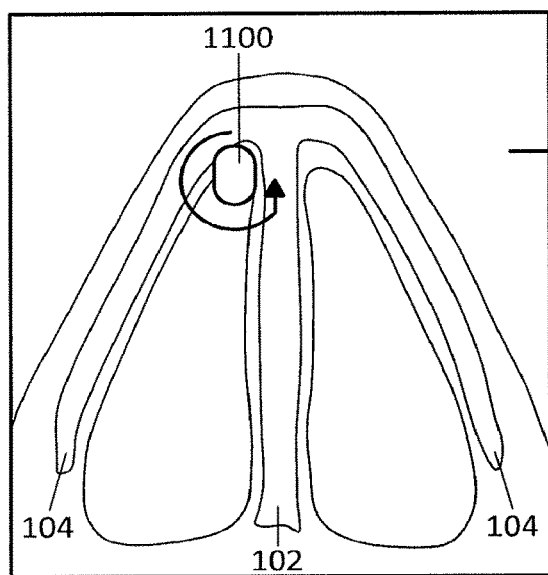
FIGS. 11A-11B show a dissection tool having an expandable blade positioned within the nasal anatomy.
Figure 11B:
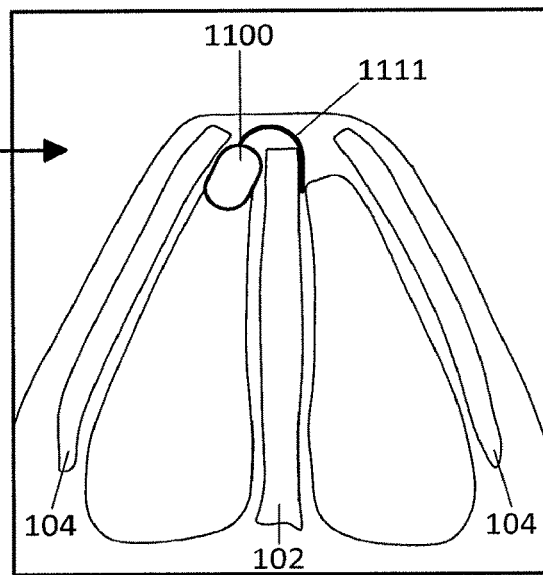

FIGS. 11A-11B illustrate a dissection tool 1100 cutting a portion of a nasal anatomy in accordance with some embodiments. The dissection tool 1100 includes a retractable blade 1111 that can be advanced or retracted by turning an actuator. The illustrated tool 1100 has a circular cross section (though can include an ovular or rectangular cross-section). The blade 1111 can be at a distal end of the tool and can be advanced from a stowed configuration in the interior portion of the tool 1100 (FIG. 11A) to an extended configuration (FIG. 11B) by turning the actuator. In some embodiments, the blade 1111 can form an arcuate or curved shape once extended. For example, as shown in FIG. 11B, the blade 1111 can be adapted with a curvature that can allow for the blade 1111 to conform to a portion of the septum 102 such that the blade 1111 and tool 1100 can be moved along the septum 102 to cut a portion of the nasal anatomy (such as the upper lateral cartilage 104). The tool 1100 can be advanced distally with the blade 1111 extended to cut the upper lateral cartilage 104 or the tool can be advanced with the blade 1111 in a retracted position followed by deploying the blade 1111 and pulling the tool 1100 proximally to the cut the nasal anatomy.

Figure 12A:
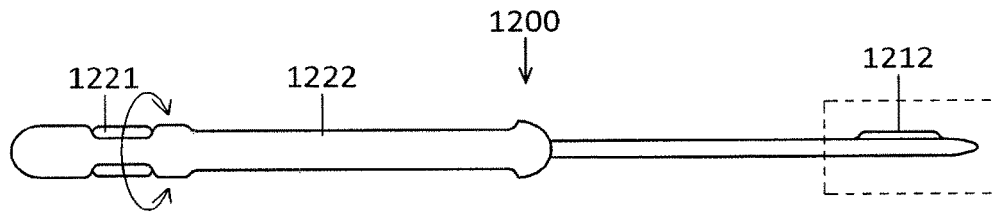
FIGS. 12A-12E show use of a dissection tool with an extendable blade.
Figure 12A:
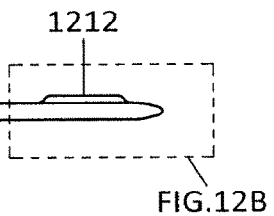
Figure 12B:
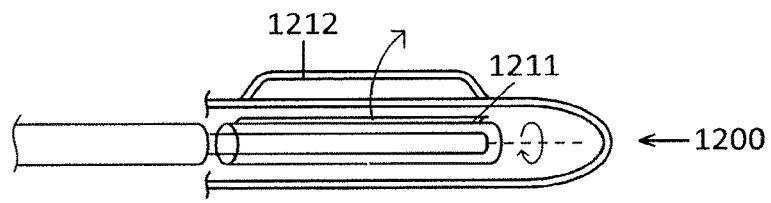
Figure 12C:
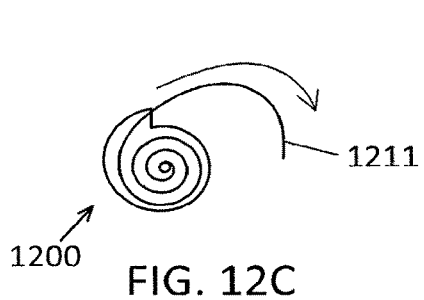
Figure 12D:
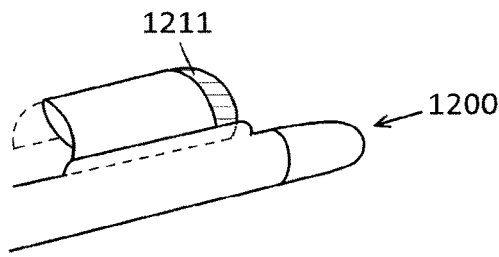
Figure 12E:
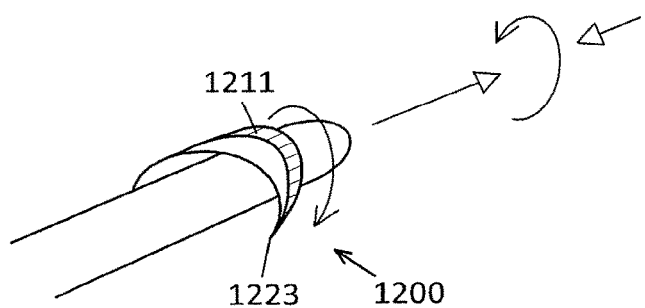

FIGS. 12A-E illustrate a minimally invasive dissection tool 1200 in accordance with some embodiments. The dissection tool 1200 includes a retractable blade 1211 that can be advanced or retracted by turning an actuator 1221 of the dissection tool 1200 (e.g., an actuator 1221 on the handle 1222). The retractable blade 1211 can be at a distal end of the tool 1200 and can be advanced out of a window 1212 or opening in the distal portion of the tool 1200. The retractable blade 1211 can have the cutting edge on a distal dimension of the blade 1211 such that tissue is cut when the tool 1200 is advanced distally. In some embodiments, a proximal edge of the retractable blade 1211 can include a cutting surface alone or in combination with a distal cutting blade 1211. In some cases the retractable blade can also have a pointed end 1223 that can pierce tissue along the axial direction along the axis that the blade 1211 is advanced from the dissection tool 1200, as shown in FIG. 12E.

Figure 13A:
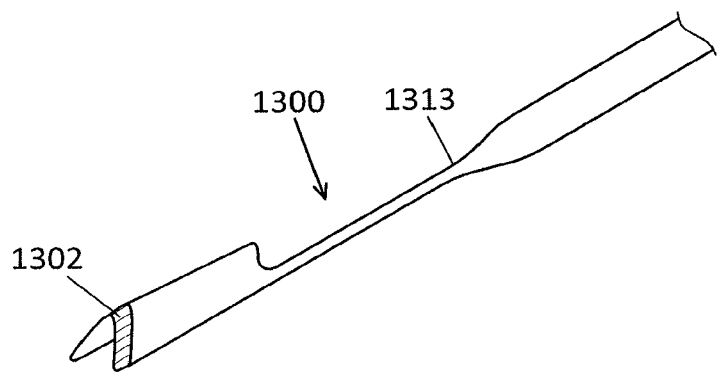
FIGS. 13-13B show a dissection tool (FIG. 13A) and the dissection tool cutting a portion of the nasal anatomy (FIG. 13B).
Figure 13B:
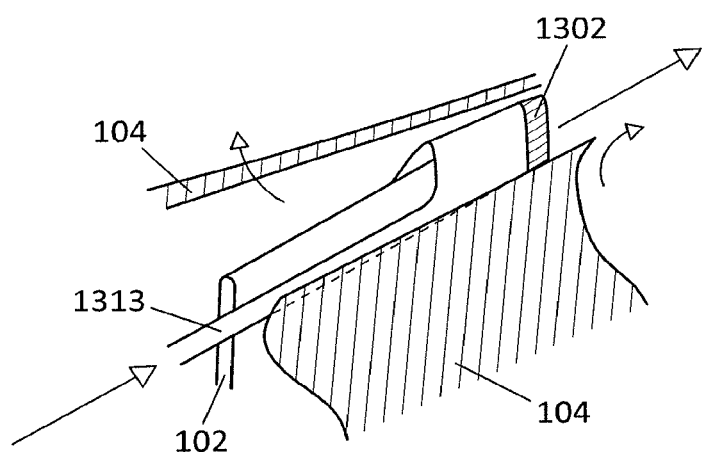

FIGS. 13A-13B illustrate a dissection tool 1300 and the dissection tool 1300 cutting a portion of a nasal anatomy in accordance with some embodiments. The dissection tool 1300 has an elongate portion 1313 and a distal blade 1302 with a V-shaped cross-sectional shape and distal cutting blade. The V-shaped blade 1302 can straddle the septum 102. When advanced along the septum 102, the blade 1302 can cut the desired nasal tissue (e.g., can cut between the septum 102 and the cartilage 104), as shown in FIG. 13B.

FIG. 17A demonstrates that, in some embodiments, an incision 1717 can be made to provide access for one or more of the dissection tools described herein. Further, FIGS. 17B-17L illustrate various dissection tools 1700b-1700l that can be used in the methods described herein in accordance with some embodiments. For example, FIG. 17B shows a dissection tool 1700b including a cutting blade 1725b with a concave edge or surface. In contrast, FIG. 17C shows a dissection tool 1700c with a cutting blade 1725c having a convex edge or surface. FIG. 17D illustrates that the dissection tool 1700d can have a curved cutting edge 1725d and two pointed tips 1715d configured to extend on either side of the septum in use. FIG. 17E shows a dissection tool 1700e having two curved cutting blades 1725e while FIGS. 17F-G show a dissection tool 1700f having two straight blades 1725f configured to extend on either side of the septum 102 (between the septum 102 and cartilage 104). FIG. 17H shows a dissection tool 1700h having two blades 1725h configured to extend axially along either side of the septum. FIG. 17I shows a dissection tool 1700i having a blade 1725i with a concave curvature and a pointed tip 1715i. FIG. 17J shows a dissection tool 1700j with a curved blade 1725j configured to confirm to one side of the septum. FIG. 17K shows a dissection tool 1700k with a spiraled cutting blade 1725k (e.g., which could be extended from a cover during use). Finally, FIG. 17L shows a dissection tool 1700l with a u-shaped cutter 1725l.

Figure 18A:
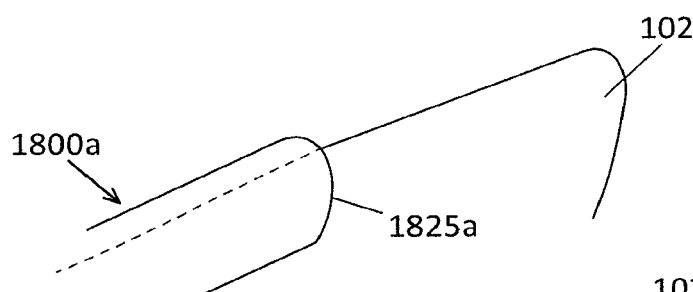
FIGS. 18A-18B show an embodiment of a dissection tool in use in the nasal anatomy.
Figure 18B:
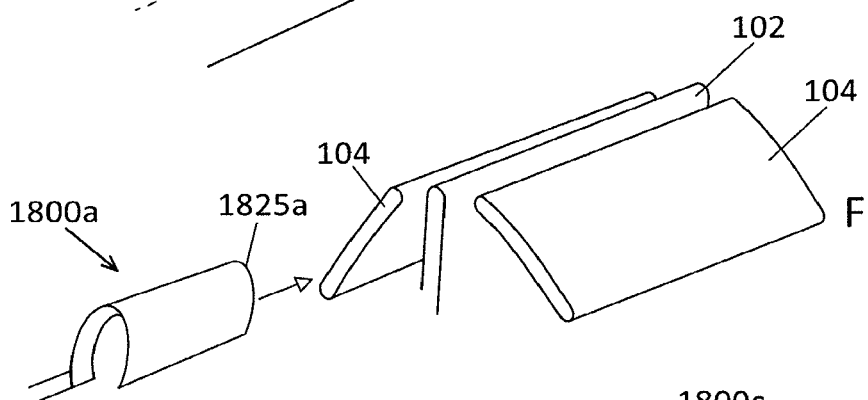
Figure 18C:
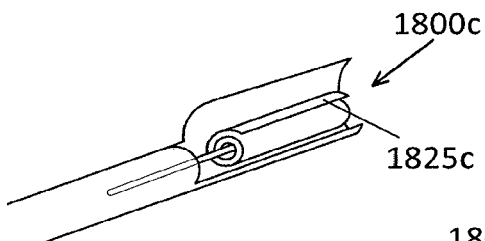
FIGS. 18C-18E show another embodiment of a dissection tool in use in the nasal anatomy.
Figure 18D:
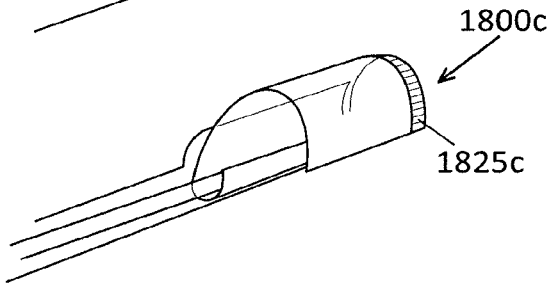
Figure 18E:
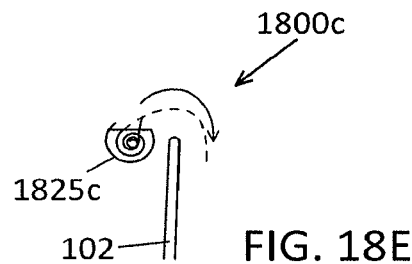

FIGS. 18A-18E illustrate various embodiments of dissection tools that can be used in the methods described herein. Referring to FIGS. 18A-18B, the dissection tool 1800a includes a blade 1825a with a curved shape that can cut tissue on both sides of the septum 102 (e.g., between the septum 102 and the cartilage 104). FIGS. 18C-18D illustrate a dissection tool 1800c having a spiral or otherwise stored curved blade 1825c. The blade 1825c can be in-situ to cut tissue adjacent to septum 102. The dissection tool 1800c can be more minimally invasive when the blade 1825c is unfurled within the body tissue, as less skin is cut upon dissection tool entry into the nasal tissue.

Figure 20A:
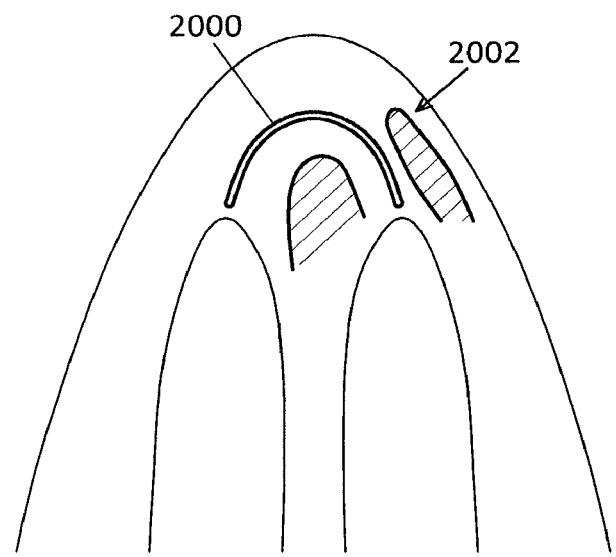
FIGS. 20A-20B show a dissection tool that can be used in the nasal anatomy.
Figure 20B:
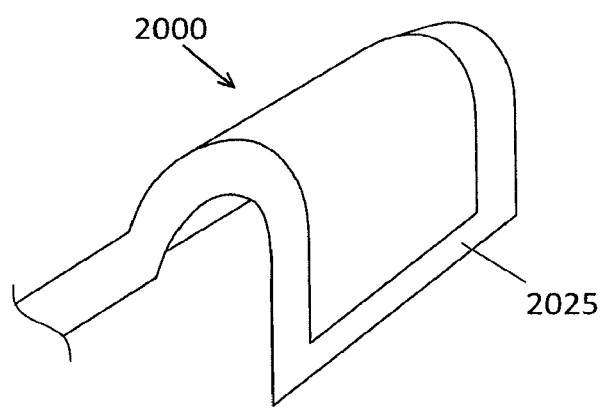

FIGS. 20A-10B illustrate a dissection tool 2000 that can be used in some embodiments with an offset cutting edge 2025. FIG. 20A shows the dissection tool 2000 cutting a portion of the nasal tissue 2002.

Figure 21:
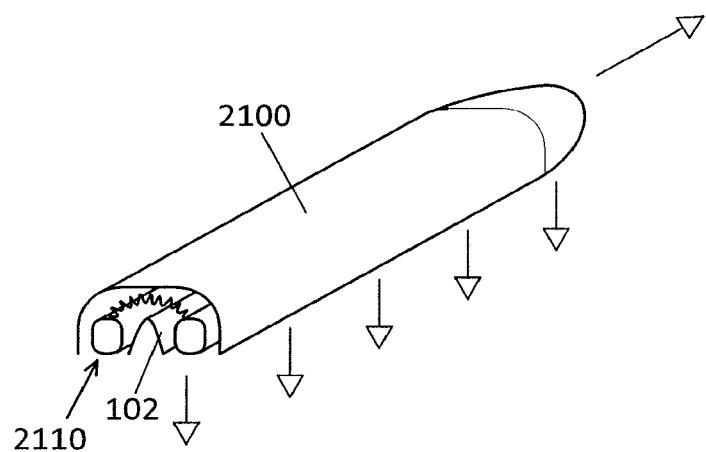
FIG. 21 shows an embodiment of a delivery tool for a nasal implant.

FIG. 21 shows a tool 2100 configured to delivery a nasal implant 2110 over the septum 102. The delivery tool 2100 can include a hollow interior configured to house the implant 2110. In some embodiments, the tool 2100 can also include a dissecting element (e.g., a blade) to cut the tissue prior to delivery and implantation.

It should be understood that any element described herein with respect to one embodiment can be combined with or substituted for any element described herein with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A nasal implant comprising:
   a first longitudinal portion having (i) a first inner surface configured to engage with a first side of a septum or a septal cartilage of a patient and (ii) a first outer surface configured to engage with an upper lateral cartilage of the patient;
   a second longitudinal portion having (i) a second inner surface configured to engage with a second side of the septum or the septal cartilage of the patient and (ii) a second outer surface configured to engage with the upper lateral cartilage of the patient; and
   a bridge portion coupling the first longitudinal portion and the second longitudinal portion, wherein the bridge portion is configured to engage with the septum or septal cartilage,
   wherein the bridge portion comprises one or more features selected from a group consisting of: a plurality of barbs, a plurality of hooks, a plurality of projections, and a suture,
   wherein the first longitudinal portion comprises a plurality of openings,
   wherein the one or more features of the bridge portion extend from the second longitudinal portion and are received in the plurality of openings of the first longitudinal portion, and
   wherein the nasal implant is sized to reside within a nasal tissue of the patient between a mucosa, the septum or the septal cartilage, and the upper lateral cartilage.

2. The nasal implant of claim 1, wherein the one or more features comprises the suture.

3. The nasal implant of claim 1, wherein the one or more features comprises a plurality of grooves.

4. The nasal implant of claim 1, wherein the bridge portion further comprises the plurality of projections.

5. The nasal implant of claim 1, wherein at least one of the first longitudinal portion or the second longitudinal portion comprises a plurality of openings adapted to receive a suture or allow tissue ingrowth.

6. The nasal implant of claim 1, wherein the first longitudinal portion and the second longitudinal portion define a U-shape or V-shape.

7. The nasal implant of claim 1, wherein the first longitudinal portion and the second longitudinal portion are made out of a bioabsorbable material.

8. The nasal implant of claim 1, wherein the first longitudinal portion and the second longitudinal portion are made out of a non-bioabsorbable material.

9. A nasal implant system comprising:
a nasal implant comprising:
  a first longitudinal portion having (i) a first inner surface configured to engage with a first side of a septum or a septal cartilage of a patient and (ii) a first outer surface configured to engage with an upper lateral cartilage of the patient;
  a second longitudinal portion having (i) a second inner surface configured to engage with a second side of the septum or the septal cartilage of the patient and (ii) a second outer surface configured to engage with the upper lateral cartilage of the patient;
  a bridge portion connecting the first longitudinal portion and the second longitudinal portion, wherein the bridge portion is configured to engage with the septum or septal cartilage,
  wherein the nasal implant is sized to reside within a nasal tissue of the patient between a mucosa, the septum or the septal cartilage, and the upper lateral cartilage; and
a dissection tool comprising:
  a proximal handle portion, and
  a distal portion extending from the proximal handle portion, wherein the distal portion comprises a cutting edge that is configured to separate cartilage or tissue from a first side of the septum and a second side of the septum,
  wherein the dissection tool is configured to deploy the cutting edge after the dissection tool has been inserted into a nasal anatomy, and
  wherein the distal portion comprises a retractable blade that is configured to advance out of an opening in the distal portion, wherein the retractable blade comprises the cutting edge.

10. The nasal implant system of claim 9, wherein the bridge portion is made out of at least one material selected from a group consisting of: a mesh material, a textile material, a sheet material, a suture, and an open cell structure.

11. A method of implanting a nasal implant in nasal tissue, comprising:
using a dissection tool to separate a cartilage or a tissue from a first side of a septum and a second side of the septum; and
positioning a nasal implant within a nasal tissue an implant site located between (i) a mucosa, (ii) the septum or a septal cartilage, and (iii) an upper lateral cartilage of a patient, wherein positioning the nasal implant comprises:
  positioning a first longitudinal portion of the nasal implant with a first inner surface engaging the first side of the septum or the septal cartilage of a patient and a first outer surface engaging the upper lateral cartilage of the patient,
  positioning a second longitudinal portion of the nasal implant with a second inner surface engaging the second side of the septum or the septal cartilage of the patient and a second outer surface engaging the upper lateral cartilage of the patient, and
  engaging a bridge portion of the nasal implant with the septum or the septal cartilage, wherein the bridge portion couples the first longitudinal portion and the second longitudinal portion.

12. The method of claim 11, wherein using the dissection tool comprises:
inserting the dissection tool in a nasal anatomy of the patient; and
after inserting the dissection tool, cutting the cartilage or the tissue.

13. The method of claim 12, further comprising after inserting the dissection tool, actuating the dissection tool to deploy a retractable blade from the a distal portion of the dissection tool.

14. The method of claim 11, wherein positioning the nasal implant within the nasal tissue supports a nasal valve and controls a cosmetic change to the nasal tissue.

15. The method of claim 11, wherein the bridge portion is made out of at least one material selected from a group consisting of: a mesh material, a textile material, a sheet material, a suture, and an open cell structure.

16. The method of claim 13, wherein actuating the dissection tool comprises actuating an actuator on a handle of the dissection tool to deploy the retractable blade out of a window in the distal portion of the dissection tool.

17. The method of claim 16, further comprising, after actuating the actuator to deploy the retractable blade, actuating the actuator on the handle to retract the retractable blade back into the distal portion of the dissection tool.

18. The method of claim 11, wherein the dissection tool comprises a cutting edge that is configured to simultaneously slide along both the first side of the septum and the second side of the septum.

19. The nasal implant system of claim 9, wherein the dissection tool comprises an actuator on the proximal handle portion, wherein the actuator is operable to deploy the retractable blade out of the opening in the distal portion.

20. The nasal implant of claim 1, wherein the one or more features comprises the plurality of hooks.

* * * * *